(12) United States Patent
Krall et al.

(10) Patent No.: US 11,903,645 B2
(45) Date of Patent: *Feb. 20, 2024

(54) METHOD AND SYSTEM FOR MEASURING BINOCULAR ALIGNMENT

(71) Applicant: Neurolens, Inc., Coppell, TX (US)

(72) Inventors: Jeffrey P. Krall, Mitchell, SD (US); Aric Plumley, Costa Mesa, CA (US)

(73) Assignee: Neurolens, Inc., Coppell, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/065,182

(22) Filed: Dec. 13, 2022

(65) Prior Publication Data
US 2023/0116898 A1    Apr. 13, 2023

Related U.S. Application Data

(63) Continuation of application No. 16/579,826, filed on Sep. 23, 2019, now Pat. No. 11,589,745, which is a
(Continued)

(51) Int. Cl.
| | | |
|---|---|---|
| *A61B 3/08* | (2006.01) | |
| *A61B 3/00* | (2006.01) | |
| *A61B 3/113* | (2006.01) | |

(52) U.S. Cl.
CPC .............. *A61B 3/08* (2013.01); *A61B 3/0041* (2013.01); *A61B 3/0091* (2013.01); *A61B 3/113* (2013.01)

(58) Field of Classification Search
CPC ....... A61B 3/08; A61B 3/0041; A61B 3/0091; A61B 3/113
(Continued)

(56) References Cited

U.S. PATENT DOCUMENTS

| | | |
|---|---|---|
| 3,245,745 A | 4/1966 | Hancock |
| 4,056,311 A | 11/1977 | Winthrop |
| | (Continued) | |

FOREIGN PATENT DOCUMENTS

| | | |
|---|---|---|
| CN | 1438852 A | 8/2003 |
| CN | 103815866 A | 5/2014 |
| | (Continued) | |

OTHER PUBLICATIONS

Bruce J.W. Evans, "Optometric Prescribing for Decompensated Heterophoria," Optometry in Practice, vol. 9, 2008, pp. 63-78.
(Continued)

*Primary Examiner* — Mohammed A Hasan
(74) *Attorney, Agent, or Firm* — Gergely T. Zimanyi

(57) ABSTRACT

Embodiments of the invention include a method to determine a binocular alignment, the method comprising: measuring a disassociated phoria of a first eye and a second eye of a patient at an apparent distance; and determining an accommodative convergence of the first eye and the second eye at the apparent distance using the measured disassociated phoria. In other embodiments, a system to determine a binocular alignment comprises a stereo display, for a projection of images for a first eye and a second eye; an accommodation optics, to modify the projection of the images according to an apparent distance; an eye tracker, to track an orientation of the first eye and the second eye; and a computer, coupled to the stereo display, the accommodation optics and the eye tracker, to manage a determination of the binocular alignment.

21 Claims, 29 Drawing Sheets

Related U.S. Application Data continuation of application No. 15/696,161, filed on Sep. 5, 2017, now Pat. No. 10,420,467.

(58) Field of Classification Search
USPC .......................................................... 351/201
See application file for complete search history.

(56) References Cited

U.S. PATENT DOCUMENTS

| | | | |
|---|---|---|---|
| 4,222,639 | A | 9/1980 | Sheedy |
| 4,240,719 | A | 12/1980 | Gunter et al. |
| 4,253,747 | A | 3/1981 | Maitenaz |
| 4,580,882 | A | 4/1986 | Nuchman et al. |
| 4,580,883 | A | 4/1986 | Shinohara |
| 4,606,626 | A | 8/1986 | Shinohara |
| 4,756,305 | A | 7/1988 | Mateik et al. |
| 4,906,090 | A | 3/1990 | Barth |
| 4,961,639 | A | 10/1990 | Lazarus |
| 5,026,151 | A | 6/1991 | Waltuck et al. |
| 5,200,859 | A | 4/1993 | Payner et al. |
| 5,305,028 | A | 4/1994 | Okano |
| 5,381,191 | A | 1/1995 | Levy |
| 5,557,348 | A | 9/1996 | Umeda et al. |
| 5,724,120 | A | 3/1998 | Svochak et al. |
| 5,728,156 | A | 3/1998 | Gupta et al. |
| 5,782,894 | A | 7/1998 | Israel |
| 5,946,075 | A | 8/1999 | Horn |
| 5,969,790 | A | 10/1999 | Onufryk |
| 6,019,470 | A | 2/2000 | Mukaiyama et al. |
| 6,062,691 | A | 5/2000 | Markson |
| 6,106,819 | A | 8/2000 | Sucher |
| 6,142,624 | A | 11/2000 | Morris et al. |
| 6,318,857 | B1 | 11/2001 | Shirayanagi |
| 6,347,869 | B1 | 2/2002 | Xu et al. |
| 6,364,481 | B1 | 4/2002 | O'Connor et al. |
| 6,505,934 | B1 | 1/2003 | Menezes |
| 6,547,387 | B1 | 4/2003 | Katsantones |
| 6,579,478 | B2 | 6/2003 | Lossman et al. |
| 6,652,097 | B2 | 11/2003 | Shirayanagi |
| 6,776,486 | B2 | 8/2004 | Steele et al. |
| 6,789,898 | B2 | 9/2004 | Le Saux et al. |
| 6,871,954 | B2 | 3/2005 | Copeland |
| 6,956,682 | B2 | 10/2005 | Wooley |
| 7,104,647 | B2 | 9/2006 | Krall |
| 7,216,977 | B2 | 5/2007 | Poulain et al. |
| 7,290,878 | B1 | 11/2007 | Hofeldt |
| 7,703,921 | B2 | 4/2010 | Dick et al. |
| 7,828,439 | B2 | 11/2010 | Krall |
| 7,976,157 | B2 | 7/2011 | Croft et al. |
| 8,042,940 | B2 | 10/2011 | Krall et al. |
| 8,100,529 | B2 | 1/2012 | Kozu |
| 8,287,124 | B2 | 10/2012 | Krall et al. |
| 8,376,546 | B2 | 2/2013 | Kozu |
| 8,425,034 | B2 | 4/2013 | Wietschorke |
| 9,237,843 | B1 | 1/2016 | Krall et al. |
| 9,274,351 | B2 | 3/2016 | Drobe |
| 9,298,021 | B2 | 3/2016 | Krall et al. |
| 10,048,511 | B2 | 8/2018 | Krall et al. |
| 10,048,512 | B2 | 8/2018 | Krall et al. |
| 10,420,467 | B2 | 9/2019 | Krall et al. |
| 11,589,745 | B2* | 2/2023 | Krall ................ A61B 3/0041 |
| 2002/0036750 | A1* | 3/2002 | Eberl ................ G02B 27/0093 351/207 |
| 2002/0051116 | A1 | 5/2002 | Van Saarloos et al. |
| 2002/0099305 | A1 | 7/2002 | Fukushima et al. |
| 2006/0092375 | A1 | 5/2006 | Menezes et al. |
| 2006/0139571 | A1 | 6/2006 | Poulain et al. |
| 2006/0170863 | A1 | 8/2006 | Krall |
| 2006/0244915 | A1 | 11/2006 | Clemons et al. |
| 2007/0182923 | A1 | 8/2007 | Kitani et al. |
| 2008/0049152 | A1 | 2/2008 | Hong et al. |
| 2008/0117289 | A1 | 5/2008 | Schowengerdt et al. |
| 2008/0278676 | A1 | 11/2008 | Croft et al. |
| 2009/0153796 | A1 | 6/2009 | Rabner |
| 2009/0153798 | A1 | 6/2009 | Dick |
| 2009/0185137 | A1 | 7/2009 | Krall |
| 2009/0290121 | A1 | 11/2009 | Drobe et al. |
| 2010/0066974 | A1 | 3/2010 | Croft et al. |
| 2010/0109176 | A1 | 5/2010 | Davison |
| 2010/0271590 | A1 | 10/2010 | Kitani et al. |
| 2011/0090455 | A1 | 4/2011 | Gupta et al. |
| 2011/0109822 | A1 | 5/2011 | Kato et al. |
| 2011/0317127 | A1 | 12/2011 | Suzuki et al. |
| 2012/0002163 | A1 | 1/2012 | Neal |
| 2012/0019774 | A1 | 1/2012 | Krall et al. |
| 2012/0019775 | A1 | 1/2012 | Tyrin et al. |
| 2012/0019776 | A1 | 1/2012 | Giraudet |
| 2012/0081661 | A1 | 4/2012 | Yamakaji |
| 2012/0200822 | A1 | 8/2012 | Kaga et al. |
| 2012/0250152 | A1 | 10/2012 | Larson et al. |
| 2012/0307203 | A1* | 12/2012 | Vendel ................ A61H 5/00 351/201 |
| 2012/0317825 | A1 | 12/2012 | Ohta |
| 2013/0010097 | A1 | 1/2013 | Durnell et al. |
| 2013/0265540 | A1 | 10/2013 | Esser et al. |
| 2013/0293531 | A1 | 11/2013 | Cao et al. |
| 2013/0308099 | A1 | 11/2013 | Stack |
| 2014/0028972 | A1 | 1/2014 | Granger et al. |
| 2014/0327875 | A1 | 11/2014 | Blum et al. |
| 2015/0049301 | A1 | 2/2015 | Krall et al. |
| 2015/0212338 | A1 | 7/2015 | Qi |
| 2015/0226983 | A1 | 8/2015 | Carmon et al. |
| 2015/0346515 | A1 | 12/2015 | Kozu |
| 2016/0073870 | A1 | 3/2016 | Bailey |
| 2016/0270656 | A1 | 9/2016 | Samec et al. |
| 2017/0148215 | A1 | 5/2017 | Aksoy et al. |
| 2017/0293356 | A1* | 10/2017 | Khaderi ................ G16H 50/20 |
| 2017/0311793 | A1* | 11/2017 | Green ................ A61B 3/113 |
| 2017/0343835 | A1 | 11/2017 | Carmon et al. |
| 2018/0136486 | A1 | 5/2018 | Macnamara |
| 2019/0069777 | A1 | 3/2019 | Krall et al. |
| 2019/0239790 | A1* | 8/2019 | Gross ................ G16H 50/70 |

FOREIGN PATENT DOCUMENTS

| | | |
|---|---|---|
| CN | 104204904 A | 12/2014 |
| EP | 2301422 A1 | 3/2011 |
| FR | 2 814 819 | 4/2002 |
| FR | 2 850 763 | 8/2004 |
| JP | 60-92730 | 5/1985 |
| JP | H10-322724 | 4/1998 |
| JP | 11-197108 A | 7/1999 |
| JP | 2002-253509 | 9/2002 |
| JP | 2011-072431 | 4/2011 |
| JP | 2012-100759 | 5/2012 |
| JP | 2016-536105 A | 11/2016 |
| WO | 2007/026368 A2 | 3/2007 |
| WO | 2007/068819 | 6/2007 |
| WO | 2008/012649 | 1/2008 |
| WO | 2011/067361 | 6/2011 |
| WO | 2012/160741 | 11/2012 |
| WO | 2013/112705 A1 | 8/2013 |
| WO | 2015/070023 A2 | 5/2015 |
| WO | 2015131399 A1 | 9/2015 |
| WO | 2016/007124 | 1/2016 |
| WO | 2016/020229 | 2/2016 |
| WO | 2016/101204 | 6/2016 |
| WO | 2016/139662 A1 | 9/2016 |
| WO | 2016/149416 A1 | 9/2016 |
| WO | 2016191709 A1 | 12/2016 |
| WO | 2017/131770 | 8/2017 |

OTHER PUBLICATIONS

Fogt et al., "Comparison of Fixation Disparities Obtained by Objective and Subjective Methods," Vision Res., vol. 38, No. 3, 1998, pp. 411-421.

Kim, et al., "The Analysis of AC/A Ratio in Nonrefractive Accommodative Esotropia Treated with Bifocal Glasses", Korean Journal Ophthalmology, vol. 26, No. 1, 2012, pp. 39-44.

E.H. Kim, et al., "The Relationship between Phoria and the Ratio of Convergence Peak Velocity to Divergence Peak Velocity," Invest. Ophthalmol. Vis. Sci., vol. 51, No. 8, Aug. 2010, pp. 4017-4027.

(56) References Cited

OTHER PUBLICATIONS

Remole et al, "Objective Measurement of Binocular Fixation Misalignment," American Journal of Optometry and Physiological Optics, vol. 63, No. 8, 1986, pp. 631-638.

Shapiro, "Parallel-Testing Infinity Balance Instrument and Technique for the Parallel Testing of Binocular Vision," Opt. and Vision Science, vol. 72, No. 12, 1995, pp. 916-923.

Teitelbaum et al., "Effectiveness of Base in Prism for Presbyopes with Convergence Insufficiency", Optometry and Vision Science, vol. 86, No. 2, Feb. 2009, pp. 153-156.

Wisnicki M.D., "Bifocals, Trifocals, and Progressive-Addition Lenses," American Academy of Ophthalmology, vol. XVII, No. Jun. 1999, pp. 1-8.

* cited by examiner

METHOD AND SYSTEM FOR MEASURING BINOCULAR ALIGNMENT

CROSS-REFERENCE TO RELATED APPLICATION

The present Application is a continuation of, and therefore claims benefit from U.S. patent application Ser. No. 16/579,826, entitled: "Method and System for Measuring Binocular Alignment", by Jeffrey P. Krall and Aric Plumley, filed on Sep. 23, 2019, which was the continuation of U.S. patent application Ser. No. 15/696,161, entitled: "Method and System for Measuring Binocular Alignment", by Jeffrey P. Krall and Aric Plumley, filed on Sep. 5, 2017, both Applications are hereby incorporated in their entirety by reference.

FIELD OF INVENTION

This invention relates generally to methods and systems for measuring vision acuity, and more particularly, to measuring binocular misalignment.

BACKGROUND

With normal vision, an individual is able to focus at objects located at different distances. Ideally, an individual is able to focus on distant objects, referred to as distance-vision, and on near objects, referred to as near-vision. The optical system of the eye uses numerous muscles to change the focus between these distances. These muscles adjust various aspects of the eye when transitioning between distance-vision and near-vision. The muscle adjustments include making subtle changes to the shape of the crystalline lens to adjust the focus of the lens, rotating the eyeballs to rotate their optical axes, and changing the size of the pupils.

Presbyopia is a natural deterioration of near vision, caused by loss of flexibility in the eye's crystalline lenses as one ages. Presbyopia can be partially compensated by wearing "reading" glasses that correct near-vision refraction errors, so that the eye does not have to focus as strongly when gazing at near objects. Presbyopic persons need different optical corrections for near-vision and for distance-vision. However, using two eyeglasses and changing them frequently is distracting. To avoid continually exchanging eyeglasses, bifocals may be used that offer different optical corrections for near-vision and for distance-vision. The transition between these two vision regions can be abrupt or gradual. The latter eyeglasses are called Progressive Addition Lenses (PALs). Abrupt change bifocals have a visible line separating the two vision regions, while PALs have no lines or edges visible between the regions with different dioptric powers.

In spite of all this progress, some types of vision-related discomforts still persist. One of these discomforts is related to a shift of habits in the modern, digital lifestyle. A large and increasing fraction of professions require workers to spend a large and increasing fraction of their working time focusing at close-distance digital interfaces, including computer screens and mobile devices. The same is true for the private lives of many, spending hours playing video games, texting and checking updates on cell phones, among others. All these professional and behavioral shifts rapidly increased the time people spend looking at digital screens, devices, displays, and monitors at a much closer distance than before. The increased time of the eye being trained at near-vision images places excessive demands on the muscles involved in near-vision, often straining them beyond the comfort zone. This can lead to fatigue, discomfort, pain, or even digitally induced migraines. Up to now, there is no widely accepted consensus on the precise causation mechanism of these digital-device related visual discomforts, pains and migraines, even though millions of patients experience these pains every day. Therefore, there is a need for glasses, or other optometric solutions than can provide relief for digital eye discomforts.

FIGS. 1-4 illustrate the basic problem of binocular misalignment. FIG. 1A illustrates that when we look at a near object, like the shown cross, our vision accommodates in two ways. First, we accommodate the optical power of our eyes 1-1 and 1-2 to image the near object at a distance L onto the retina of each eyes. This is often called the accommodative response A. Second, we rotate our eyes 1-1 and 1-2 inward by an angle $\alpha$, so that the visual axes 2-1 and 2-2 of the eyes are pointing at the same near object. This response is often called the accommodative convergence AC. For obvious geometric reasons, the angle $\alpha$ of the accommodative convergence AC, relative to the straight forward reference axis, is directly related to the distance L of the accommodative response A: $\alpha=\alpha(L)$. For healthy, well-aligned eyes the ratio of the accommodative convergence AC to the accommodative response A, AC/A, is a geometrically well-defined function, depending on the object distance L and the pupil distance PD of the two eyes.

FIGS. 1B-C illustrate that eyes often display various forms of accommodative misalignments. In FIG. 1B, the two eyes each turn inward, but to a lesser degree that geometry would require. This leads to the accommodative convergence angle $\alpha$ being less than geometrically necessary by a misalignment angle $\beta$. In some detail, the visual axes of the eyes 2-1 and 2-2 should point into the direction denoted as the necessary accommodative alignment to properly see the near object, but, instead, they turn inward to a lesser degree and instead point to the direction denoted as relaxed or natural accommodative alignment.

FIG. 1C illustrates a case, when this lesser turn is asymmetrical. In the shown case, the visual axis 2-1 of the first eye 1-1 properly points to the direction of the necessary accommodative alignment, while the visual axis 2-2 of the second eye 1-2 is turned inward only to the direction of the relaxed or natural accommodative alignment, that is misaligned by the accommodative misalignment angle $\beta$.

FIGS. 2A-D illustrate some types of accommodative misalignments. The definitions of misalignments used by different schools of optometry and by monographies show some discrepancies, and the techniques to characterize these misalignments are also varied. Therefore, the here-shown definitions are meant to be illustrative only, and analogues and equivalents are also within the scope of the illustrated terms.

To place the discussed misalignments into proper context, first the concept of fusing images is introduced. When our two eyes look at the same object, each eye creates its own visual perception. These perceptions are relayed from the eyes to the visual cortex, where the brain fuses the two images and creates a three dimensional (3D) perception of the viewed object. With optometric diagnostic systems, it is possible to test this image fusing. For example, two separate objects of the same shape can be separately projected into the two eyes with deflections, prisms, and mirrors that make the two projections appear to come from a single object. These visual perceptions will be fused by the brain into a perceived single image. Objects projected in this manner are called fusible objects, presenting fusible images.

If in an experiment the distance between the two objects is increased, or the deflection angles are increased, or the shapes of the objects are modified, then the projections into the two eyes start to differ. At some distance, or difference, between the objects, the discrepancy between the visual perceptions of the two eyes exceeds a threshold, and the brain stops fusing the two images into a single perception. Objects with such difference in distance, angle, or shape are called non-fusible objects, presenting non-fusible images.

With this preparation, FIGS. 2A-D illustrate the concept of fixation disparity, as measured by a test device, often called the Mallet box. The Mallet box displays two vertically aligned bars, and an "X O X" horizontal "anchor". In some implementations, the two bars can be shifted sideways. In others, adjustable mirrors or prisms are placed in front of the patient's eye to achieve the same horizontal shift. With appropriate selective optics, the anchor and only one of the bars is shown for the first eye 1-1 as a centered bar 5-1-$c$, and the same anchor plus only the other bar is shown for the second eye 1-2 as a centered bar 5-2-$c$. The anchor and the centered bars 5-1-$c$ and 5-2-$c$ are clearly fusible. Accordingly, the brains of patients without accommodative misalignment problems will properly fuse these images.

FIG. 2B illustrates that patients with accommodative misalignments will not fuse the images properly. What is typically observed is that, while the images of the anchor, seen by both eyes, are properly fused into a single image, the bars are perceived as shifted. The first eye 1-1 perceives a shifted bar 5-1-$s$, while the second eye 1-2 perceives a shifted bar 5-2-$s$. The angle $\gamma$ between the line to the image center and one of the visual axes 2-1 and 2-2 is called fixation disparity.

FIGS. 2C-D illustrate ways to measure the angle needed to counteract, or compensate the fixation disparity. In the system of FIG. 2C, the two bars are counter-shifted. A counter-shifted bar 5-1-$x$ is shown for the first eye 1-1, and a counter-shifted bar 5-2-$x$ is shown for the second eye 1-2. The bars are counter-shifted until the patient perceives the two bars as aligned. The angle corresponding to these counter-shifts, $\gamma^*$, between the visual axes and line to the counter-shifted bars is measured and is typically referred to as an associated phoria. In the system of FIG. 2D, the bars are not counter-shifted. Instead, adjustable, or exchangeable prisms 7 are inserted in front of the patient's eyes. These prisms are adjusted or exchanged until the two bars are perceived as aligned by the patient. Then the prism angles, or the refraction angles of the refracted visual axes, are reported as the associated phoria $\gamma^*$.

FIG. 3 illustrates how increasing a partial associated phoria partially compensates fixation disparity. Strictly speaking, the (full) associated phoria, that fully compensates fixation disparity, is given by the intersect of this curve with the partial associated phoria axis. If human vision were a purely optical process, the partial associated phoria would be simply equal to the negative of the partially compensated fixation disparity. Accordingly, the curve would be a straight line through the origin, tilted by −45 degrees, pointing from the upper left corner to the lower right corner. However, FIG. 3 illustrates that human vision is much more complex, and perception and image processing play crucial roles in it. FIG. 3 shows four types of relations between the partially compensated fixation disparity and the partial associated phoria. Visibly, none of these lines are straight, none of them go through the origin, and two of them don't even intercept the horizontal axis. These type II and III relations mean that no amount of partial associated phoria can compensate the fixation disparity in full. Therefore, it remains a substantial challenge to determine the associated phoria that fully compensates a patient's fixation disparity. A convention is mentioned in closing: the fixation disparity is referred to as "exo", if the eyes do not turn inward to the necessary degree, while it is referred to as "eso" in those rare cases, when the eyes turn inward too much.

FIGS. 4A-C illustrate a related visual misalignment called disassociated phoria. To characterize disassociated phoria, an experiment similar to that in FIGS. 2A-D can be carried out, with the difference that instead of showing fusible images 5-1 and 5-2, the optometrists show non-fusible images 6-1-$s$ and 6-2-$s$ for the first eye 1-1 and the second eye 1-2. In FIG. 4A, these non-fusible images are the cross and the bar. As FIG. 4B illustrates, once the eyes are unable to fuse the images, often one or both of the visual axes rotate outward. In the shown asymmetric case, the visual axis 2-2 of the second eye 1-2 rotates outward by an accommodative misalignment angle $\delta$. This angle $\delta$ of the outward rotation is measured and called disassociated phoria. In various applications, as below, the disassociated phoria is distributed over the two eyes evenly, thus the disassociated phoria per eye equaling $\delta/2$. In some cases, e.g. as illustrated in FIG. 1C, the disassociated phoria $\delta$ may manifest itself unevenly and has to be distributed between the eyes accordingly.

FIG. 4C shows a particularly clear case, when simply no image is shown for the second eye 1-2, the view of the second eye 1-2 is blocked. This is an extreme case of non-fusible images. As for FIG. 4B, in response to the block, the visual axis 2-2 of the second eye 1-2 rotates outward by a measurable disassociated phoria angle $\delta$.

As a quantitative characterization of accommodation misalignments, including fixation disparity and disassociated phoria, several practitioners use the misalignment-impacted AC/A ratio. The AC/A is a ratio of the accommodative convergence angle reduced by the fixation disparity, $\alpha-\delta/2$, (expressed with its tangent, in terms of "prism diopters" $\Delta$), divided by the accommodative distance L, expressed in diopters D. A typical definition of AC is AC=100 tan($\alpha-\delta/2$), in terms of prism diopters. For an average visual performance, an AC/A ratio of 6-6.5 $\Delta$/D is necessary, while, remarkably, in large population segments the average of the misalignment-impacted AC/A ratio was measured to be about 3.5 $\Delta$/D. Clearly, various forms of accommodative misalignment affect a large percentage of the population, and any progress towards relief from this is highly valuable.

A startling fact of the corresponding field of optometry is that the associated phoria angles and the disassociated phoria angles, determined by experienced practitioners, show remarkably wide variations. Experiments carried out on the same patient by different optometrists, and sometimes even by the same optometrist at different times, report phoria angles, expressed in prism diopters $\Delta$, with a distribution having a standard deviation as much as 3$\Delta$. (A prism diopter of 1$\Delta$ corresponds to a 1 cm prism refraction at 1 meter distance). The large variability of these methods precludes the effective determination and compensation of accommodative misalignments.

This exceptionally large standard deviation is probably due to several factors. These include the followings. (1) The methods of determination use the patient's subjective responses as key inputs. (2) Some methods use central images, while others use peripheral images for determining the associated phoria. The relative accuracy and relevance of these methods was not yet critically evaluated. (3) Most practitioners use a single measurement, or a single method, thus not benefiting from possibly important medical information that can be gleaned from carrying out multiple tests.

(4) In a previous exploratory project, Applicants also discovered that the prismatic reaction of the eyes is quite different for moving test images. However, understanding the relation of optimal prismatic corrections based on static and moving test images is in its early stages. (5) While there are several ways to define prismatic misalignments, and they produce different prismatic predictions and diagnoses, eventually a single prism needs to be formed in the spectacles. It is far from obvious how to convert and combine the various diagnostically determined prismatic corrections into a single prism prescription. Applicants are not aware of a critical study that would have evaluated how the efficacy and variability of prism prescriptions depended on the possible combinations of the determined prismatic corrections.

For all of the above reasons, determining the prismatic power that optimally compensates accommodative misalignments remains a pressing medical need.

SUMMARY

To address the above described medical needs, some embodiments of the invention include a method to determine a binocular alignment, the method comprising: measuring a disassociated phoria of a first eye and a second eye of a patient at an apparent distance; and determining an accommodative convergence of the first eye and the second eye at the apparent distance using the measured disassociated phoria.

In other embodiments, a system to determine a binocular alignment comprises a stereo display, for a projection of images for a first eye and a second eye; an accommodation optics, to modify the projection of the images according to an apparent distance; an eye tracker, to track an orientation of the first eye and the second eye; and a computer, coupled to the stereo display, the accommodation optics and the eye tracker, to manage a determination of the binocular alignment.

DETAILED DESCRIPTION

The systems described in the present patent document address the above articulated medical needs at least in the following aspects. (1) The described system and method determine the prismatic corrections only by objective measurements, without subjective input from the patient. This aspect alone greatly reduces the patient-to-patient and practitioner-to-practitioner variations of the results. In fact, studies on large samples of patients using Applicant's system and method determined prismatic corrections with a standard deviation reduced from the above mentioned 34 to well below 14. This significant reduction of the results' standard deviation alone established the here-described method to the status of quantitatively predictive diagnostic methods. (2) The system and method use both central and peripheral test images, because of a newly developed understanding of how the peripheral and the central prismatic corrections are connected. Therefore, the described system and method is a promising platform to determine an optimal compromise prismatic prescription that strikes the best compromise for compensating both central and peripheral accommodative misalignments. (3) The described method has two stages, thus it determines the eventual prismatic correction in a second stage by building on the important misalignment information acquired in the first stage. As such, the method integrates knowledge determined by different methods and benefits from the information determined by all of them. (4) One of the stages of the method involves moving test images. Therefore, the eventually determined prismatic corrections capture and integrate the dynamic prismatic response of the eye as well. (5) The reliable repeatability and small variability of the above mentioned large scale study provided a compelling argument that Applicants' method combined the outputs of different methods in an objective and effective manner to produce a single optimized and objective prismatic correction. The here-described five aspects provide advantages individually and in combinations.

FIGS. 5-10 illustrate a system 10 for determining a binocular alignment, and FIGS. 11-16 illustrate a corresponding method 100 for determining the binocular alignment.

Figure 5:
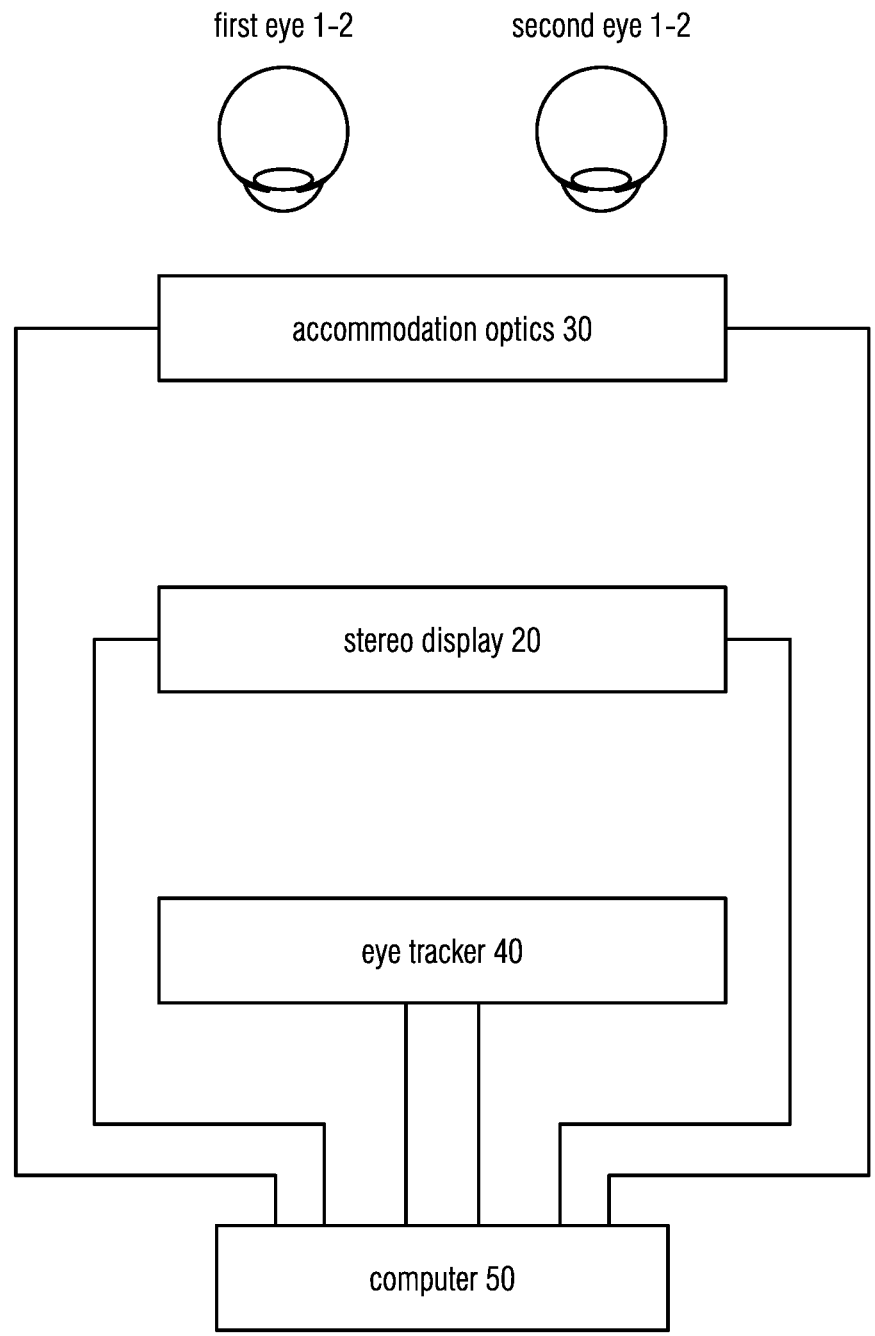
FIG. 5 illustrates a system for determining a binocular misalignment.

FIG. 5 illustrates that in some embodiments, the system 10 for determining a binocular alignment can comprise a stereo display 20, to project visible images for a first eye 1-1 and a second eye 1-2; an accommodation optics 30, to modify the projected visible images according to an apparent distance; an eye tracker 40, to track an orientation of the first eye 1-1 and the second eye 1-2; and a computer 50, coupled to the stereo display 20, the accommodation optics 30 and the eye tracker 40, to manage a determination of the binocular alignment. In what follows, the eyes will be labeled as first eye 1-1 and second eye 1-2. This labeling can correspond to a left eye and a right eye, or vice versa.

Figure 6A:
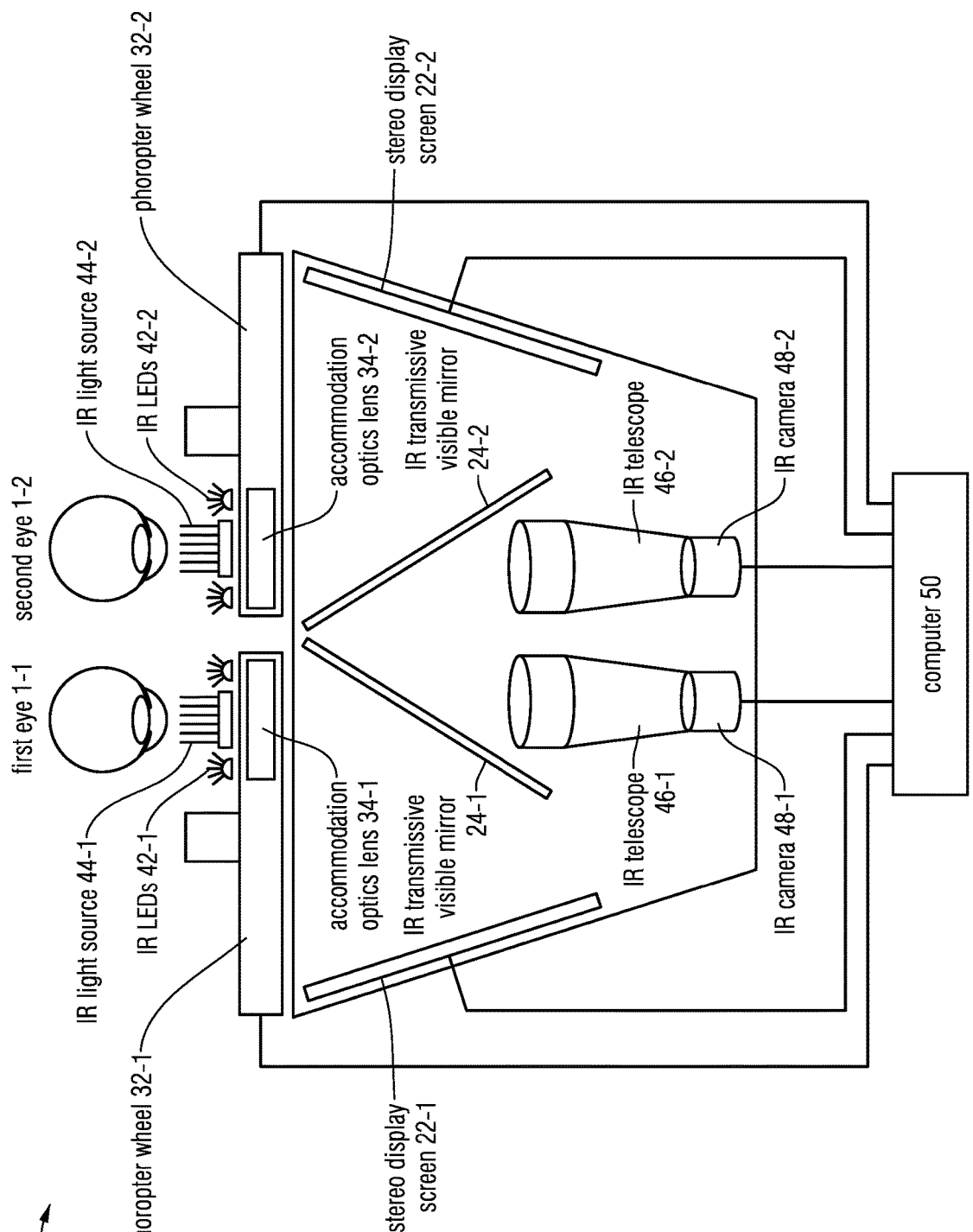
FIGS. 6A-B illustrate an embodiment of the system for determining a binocular misalignment.

FIG. 6A shows a detailed illustration of some embodiments of the system 10. In some embodiments, the eye tracker 40 can include infrared light emitting diodes, or IR LEDs, 42-1 and 42-2, positioned close to a front of the system 10, to project infrared eye-tracking beams on the first eye 1-1 and the second eye 1-2, as well as infrared light sources 44-1 and 44-2, to illuminate the first eye 1-1 and the second eye 1-2 with an infrared imaging light. The infrared eye-tracking beams and the infrared imaging light get both reflected from the eyes 1-1 and 1-2. The eye tracker 40 can further include infrared (IR) telescopes 46-1 and 46-2, with infrared (IR) cameras 48-1 and 48-2, to detect the infrared eye-tracking beams and the infrared imaging light, reflected from the first eye 1-1 and the second eye 1-2.

Many of the elements of the system 10 are included in pairs, e.g., the infrared telescopes 46-1 and 46-2. For simplicity of presentation, such pair of elements will be referred to only by their lead identifiers where doing so does not lead to misunderstanding, such as "the infrared telescope 46", abbreviating "the infrared telescopes 46-1 and 46-2."

Figure 7:
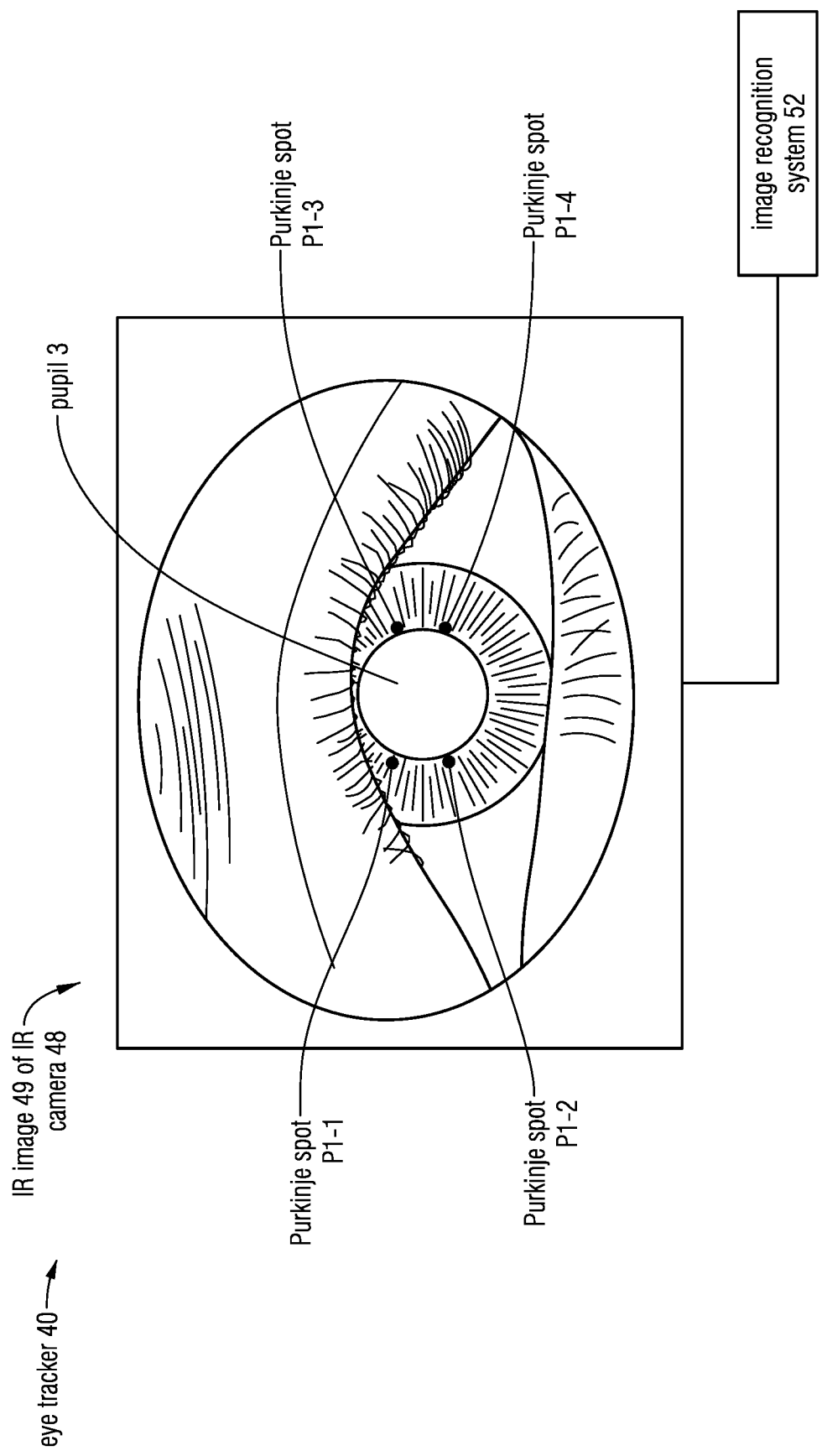
FIG. 7 illustrates an IR image by the eye tracker.

FIG. 7 illustrates a resulting IR image 49, as detected, or sensed, by the IR camera 48. In this embodiment, there are four IR LEDs 42-1, . . . 42-4 for each eye separately. To avoid clutter, the "–1" or "–2" indicating a particular eye, is omitted in the description of FIG. 7. The "–1" . . . "–4" notation here refers to the four IR LEDs, all projecting IR eye tracking beams onto the same eye. The four IR LEDs 42-1, . . . 42-4 project four IR eye-tracking beams onto the eye, which reflect from the cornea, creating four so called Purkinje spots P1-1, . . . P1-4 in the IR image 49. The "P1" notation refers to the reflection from the proximal surface of the cornea. The higher indexed Purkinje spots P2, . . . refer to reflections from deeper lying surfaces inside the eye, such as reflections from the proximal and distal surfaces of the capsule. The here-described embodiments utilize the P1 Purkinje spots, while other embodiments may employ higher indexed Purkinje spots.

The reflected IR imaging light of the IR light source 44 is detected by the IR camera 48 as well. The four Purkinje spots P1-1, . . . P1-4 overlaid on the detected reflected IR imaging light together form the IR image 49, as shown.

In some embodiments, the eye tracker 40 can include an image recognition system 52, to determine an orientation of the first eye 1-1 and the second eye 1-2, using the detected infrared eye tracking beams, forming the Purkinje spots P1-1, . . . P1-4, and the detected infrared imaging light, together forming the IR image 49. The image recognition system 52 can extract, for example, an image of the contour of a pupil 3, using edge-recognition methods. Then it can determine an orientation of the eye 1 from the center of the pupil 3. Separately, it can determine the orientation of the eye from the Purkinje spots P1-1, . . . P1-4. Finally, it can employ a weighing algorithm to determine a "best result" orientation by combining the two determined orientations, using various well known image recognition and analysis techniques. The image recognition system 52 can be a separate processor, a separate application specific integrated circuit, or it can be implemented as a software deployed in the system-managing computer 50.

Figure 6B:
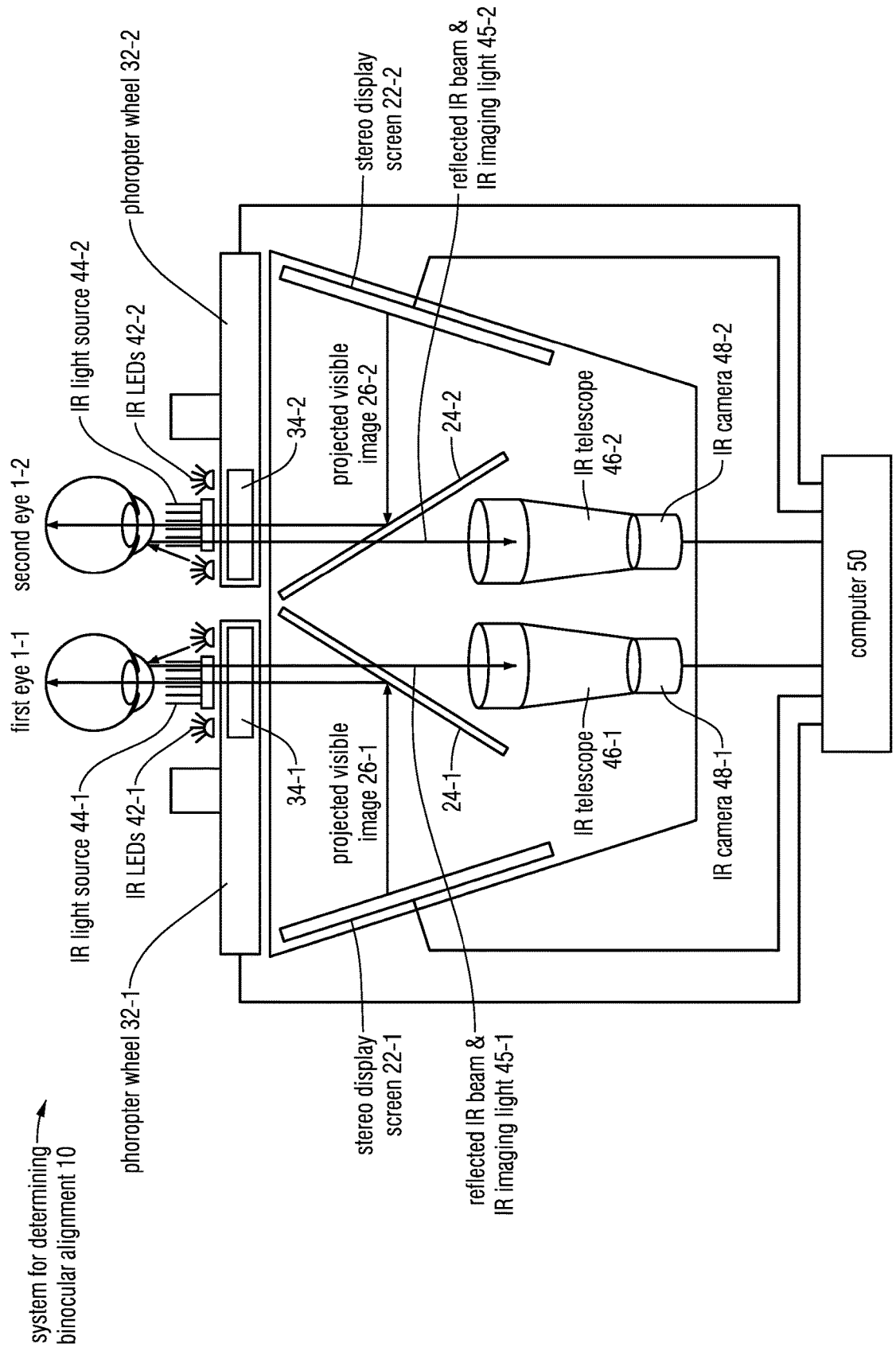

FIGS. 6A-B illustrate that the system 10 can further include infrared-transmissive visible mirrors 24-1 and 24-2, one for each eye, to redirect the projected visible images 26-1 and 26-2, from the stereo display 20 to the first eye 1-1 and the second eye 1-2; and to transmit the reflected infrared eye tracking beam and the infrared imaging light, together 45-1 and 45-2, from the first eye 1-1 and the second eye 1-2. In these embodiments, stereo display screens 22-1 and 22-2 of the stereo display 20 can be positioned peripheral to a main optical pathway of the system 10, and the infrared telescopes 46-1 and 46-2 of the eye tracker 40 can be positioned in the main optical pathway of the system 10. For reference, the accommodation optics lenses 34—mirror 24—IR telescope 46 axis for each eye is typically referred to as the main optical pathway in this embodiment. Also, for clarity's sake, in figures where the optical paths and beam are shown, some labels have been simplified.

FIG. 6B shows that in this embodiment, the peripheral stereo display screens 22-1 and 22-2 can project visible images 26-1 and 26-2 towards the main optical pathway of the system 10, that are redirected by the infrared-transmissive visible mirrors 24-1 and 24-2 toward the eyes 1-1 and 1-2. At the same time, the reflected IR eye tracking beams and the reflected IR imaging lights, together 45-1 and 45-2, reflected from the eyes 1-1 and 1-2, are transmitted by the same infrared-transmissive visible mirrors 24-1 and 24-2 toward the IR telescopes 46-1 and 46-2 along the main optical pathway of the system 10.

Figure 8A:
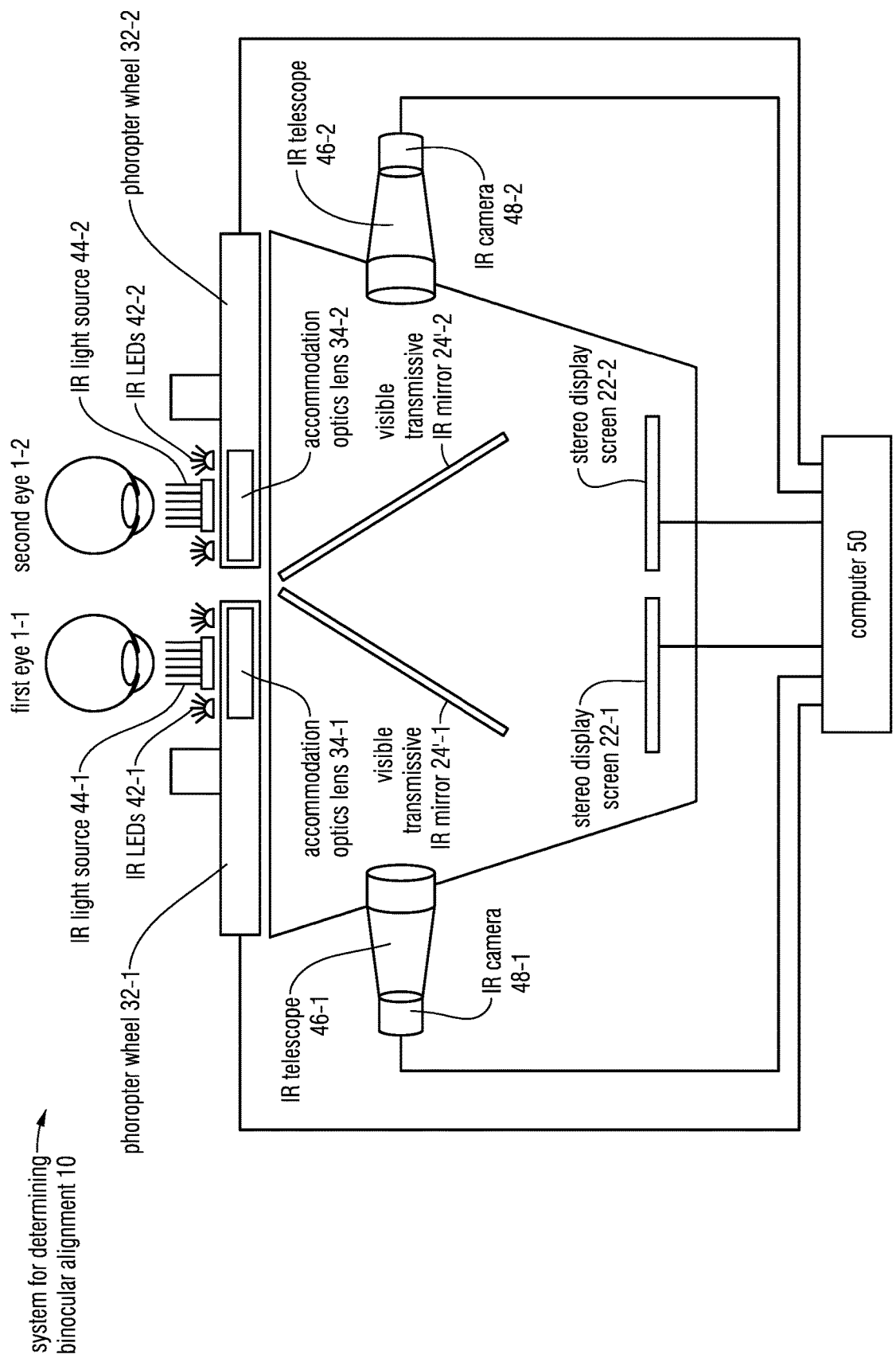
FIGS. 8A-B illustrate an embodiment of the system for determining a binocular misalignment.
Figure 8B:
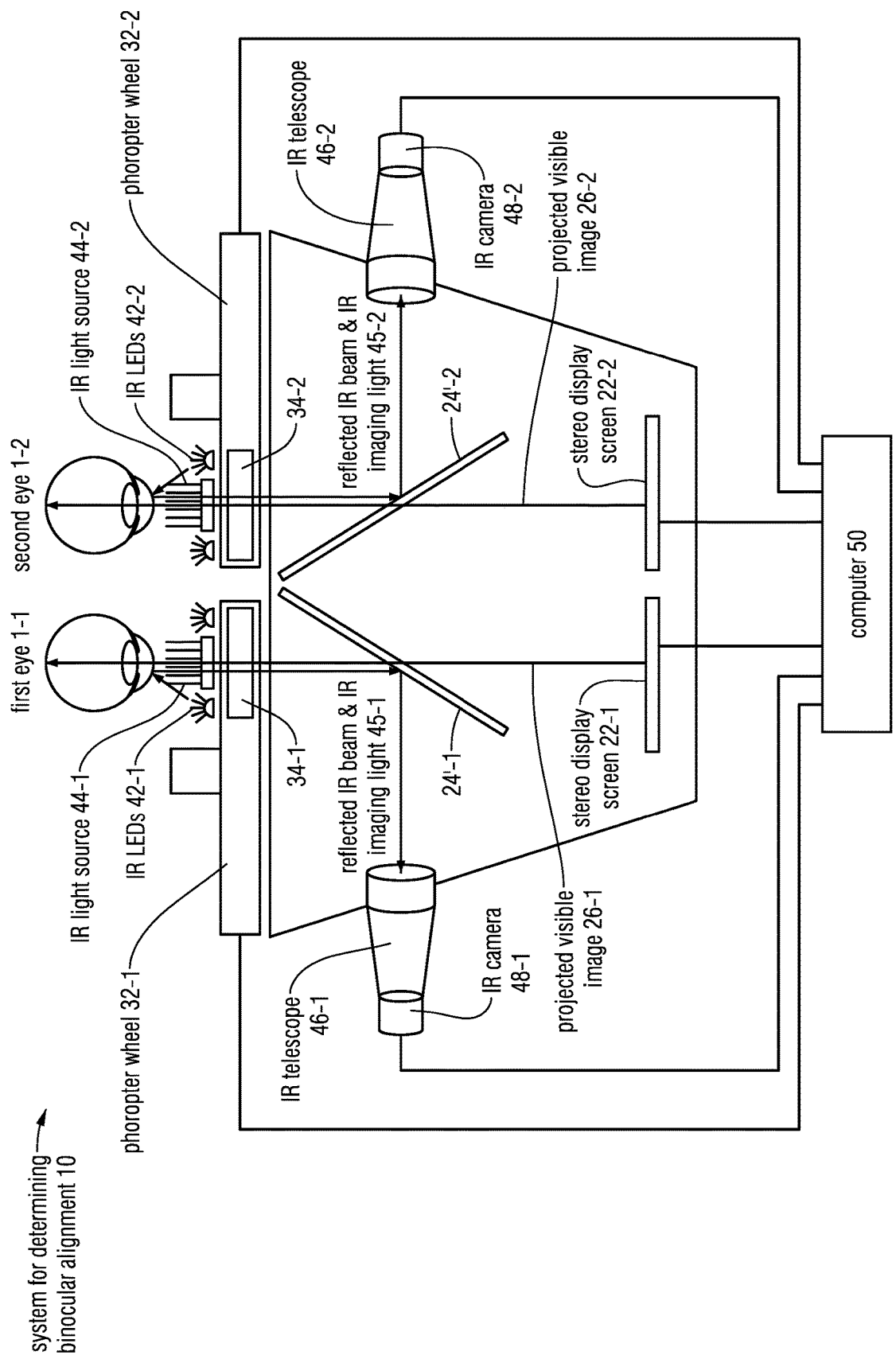

FIG. 8A illustrates another embodiment, where the location of the stereo display screens 22 and the IR telescopes 46 is exchanged. FIG. 8B illustrates that this embodiment can include visible-transmissive infrared (IR) mirrors 24'-1 and 24'-2, to redirect the reflected infrared eye tracking beam and the reflected infrared imaging light, together 45-1 and 45-2, reflected from the first eye 1-1 and the second eye 1-2, toward the IR telescopes 46-1 and 46-2. At the same time, the visible-transmissive infrared mirrors 24'-1 and 24'-2 can transmit the projected visible images 26-1 and 26-2, from the stereo display screens 22-1 and 22-2 of the stereo display 20 to the first eye 1-1 and the second eye 1-2. In these embodiments of the system 10, the stereo display 20 can be positioned in the main optical pathway of the system 10, and the infrared telescopes 46 of the eye tracker 40 can be positioned peripheral to the main optical pathway of the system 10. For reference, in this embodiment, the accommodation optics lenses 34—mirror 24—stereo display screen 22 axis for each eye is typically referred to as the main optical pathway in this embodiment.

Figure 9:
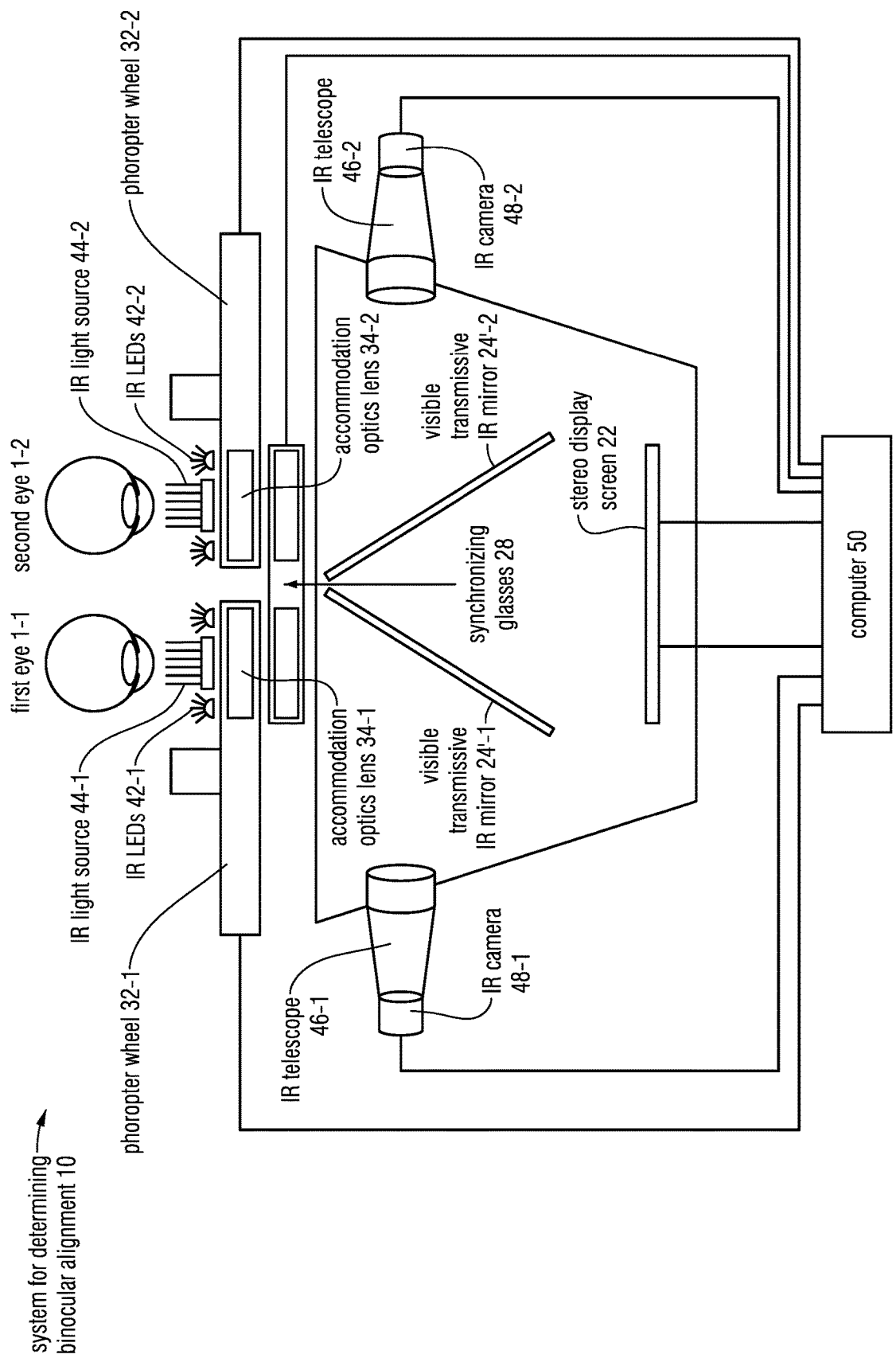
FIG. 9 illustrates an embodiment of the system for determining a binocular misalignment.

FIG. 9 illustrates a variant of the system 10 of FIGS. 8A-B, in which the stereo display 20 can include a single stereo display screen 22, and synchronizing glasses 28. The synchronizing glasses 28 can be shutter glasses or polarized glasses. In this embodiment, the projected visible images 26-1 and 26-2 of the left and right stereo display screen 22-1 and 22-2 of FIGS. 8A-B are both displayed by the single stereo display screen 22 in a rapidly alternating sequence. The synchronizing glasses 28 can be precisely coordinated with this alternating sequence, allowing the projection of the visible images 26-1 and 26-2 to the first eye 1-1 and the second eye 1-2 in a rapidly alternating manner, creating the impression of separate images being projected into these eyes. The synchronizing glasses 28 can be analogous to the 3D glasses used in the projection of 3D movies, and can rely on liquid crystal LCD layers that can rapidly change the circular polarization of the two lenses of the synchronizing glasses 28. Such systems 10 can achieve smaller footprints for the system 10 that can be advantageous. For optimal operations, a sufficiently wide field of view for the stereo display screen 22 can be helpful.

Some embodiments of the system 10 do not need to include the mirrors 24 or 24'. In these systems, the eye tracker 40 may include small implementations of the IR cameras 48, positioned close to the front of the system 10, slanted at a sufficiently large angle so that the IR cameras 48 do not block the projections by the stereo display screens 22. The image recognition system 52 of such implementations of the eye tracker 40 can include a geometric transformation unit to determine the direction of the eye visual axes from a substantially slanted IR image 49 and Purkinje spots P1, . . . P4, possibly some spots even being obscured by the slant.

In embodiments of the system 10, the accommodation optics 30 can include phoropter wheels 32-1 and 32-2 with a series of accommodation optics lenses 34-1 and 34-2 of varying optical power. These accommodation optics lenses 34 are useful to simulate the apparent distance for the first eye 1-1 and the second eye 1-2.

As described below in relation to the method 100, the system 10 can be employed to project visible images 26 at different apparent distances for a patient. Doing so can involve at least two technical solutions. First, inserting the accommodation optics lenses 34 with their variable optical power into the main optical pathway can create the impression of the projected visible images 26 being farther or closer. Second, projecting the visible images 26-1 and 26-2 closer or farther from each other can simulate an appropriate vergence of these images, another important factor in making these images appear as being at the apparent distance for the patient.

In some embodiments, for the first technical solution, the accommodation optics 30 can include, in place of the phoropter wheel 32, or in combination with the phoropter wheel 32, curved mirrors, trial lenses, flip in/flip out lenses, adjustable liquid lenses, deformable mirrors, z-directionally movable mirrors, rotating diffractive optical elements, translating diffractive optical elements, variable focus moire lenses, or focusing lens groups.

Figure 10B:
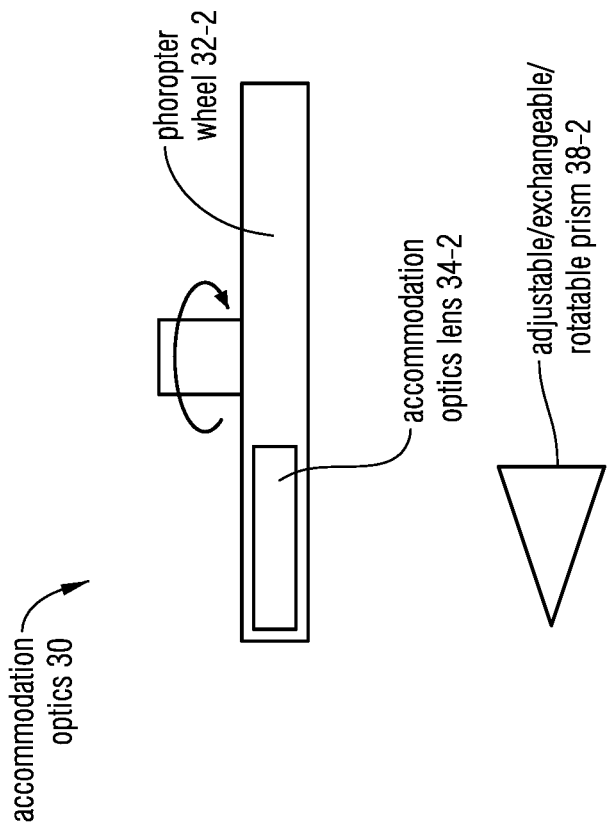
FIGS. 10A-B illustrate embodiments of the accommodation optics.
Figure 10A:
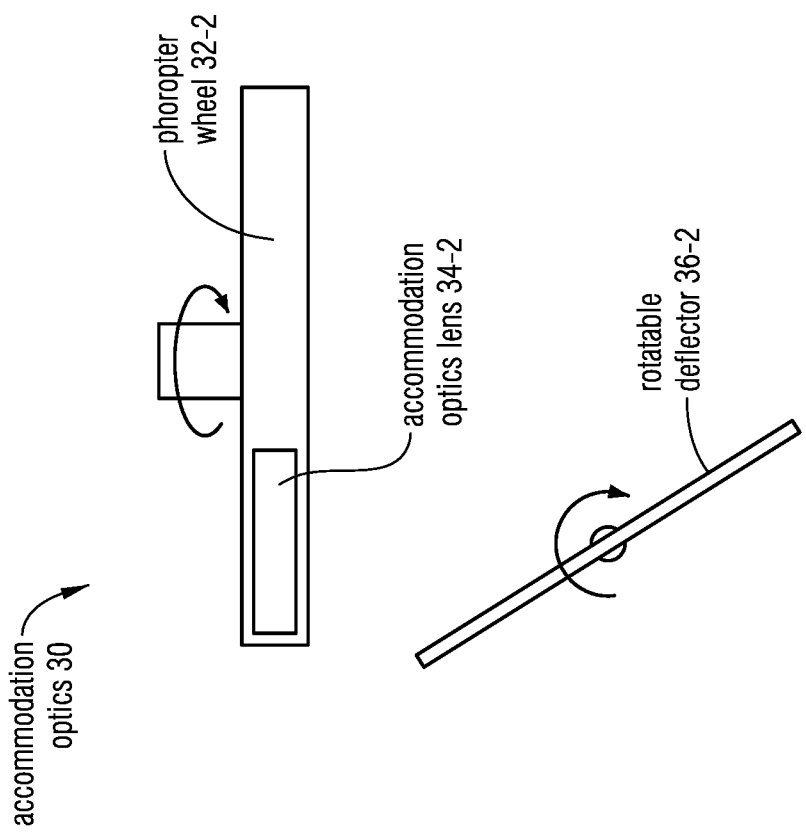

FIGS. 10A-B illustrate that for the second technical solution, the accommodation optics 30 can include a pair of rotatable deflectors 36, rotatable prisms 38, or adjustable prisms 38 (only one shown), to deflect the projection of the images 26-1 and 26-2 to the first eye 1-1 and the second eye 1-2, to simulate a vergence of the apparent distance for the first eye and the second eye.

In some embodiments, the vergence can be simulated not by the above optical elements, but by shifting the projecting of the projected visible images 26-1 and 26-2 with the stereo display screens 22-1 and 22-2 towards each other, in other words, projecting them closer to each other.

In some systems 10 the accommodation optics 30 and the stereo display 20 can be combined into a single light field display that includes a microlens array, where the projected visible images 26-1 and 26-2 shown on the stereo display screens 22-1 and 22-2, combined with the optical characteristics of the microlens array can be used to vary the apparent distance of the projected visible images 26-1 and 26-2 as seen by a patient.

In some systems 10, the accommodation optics 30 and the stereo display 20 can be combined into a single light field display that includes a mems scanner, a focus modulator, or a light source.

Having described the problem of prismatic or accommodative misalignments and embodiments of the system 10 that were developed to provide progress in the context of the misalignment problems, next, various methods 100 will be described for determining binocular misalignments using embodiments of the system 10.

FIGS. 11-16 illustrate a method 100 of how to use the above described embodiments of the system 10 to determine a binocular alignment of the eyes 1-1 and 1-2.

Figure 11:
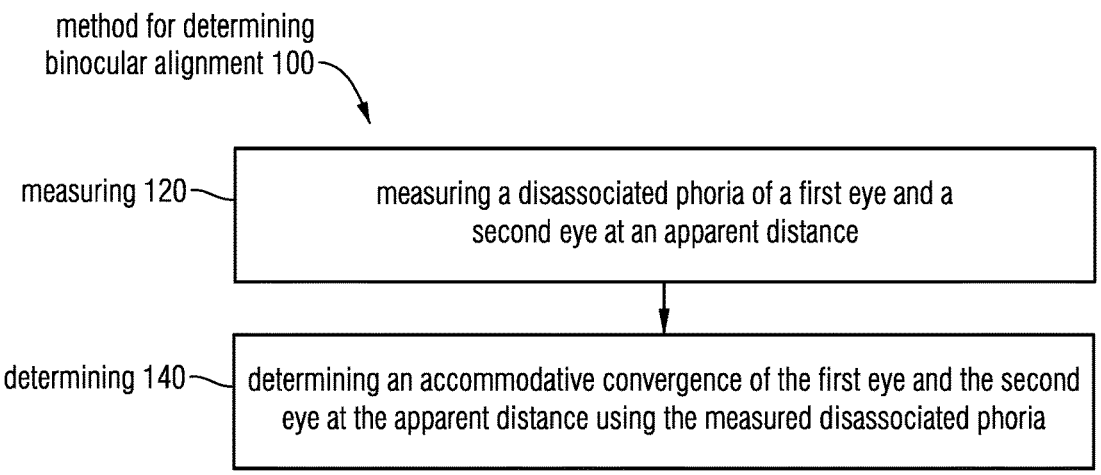
FIG. 11 illustrates a method for determining a binocular misalignment.

FIG. 11 illustrates that some embodiments of the method 100 can include a measuring 120 of a disassociated phoria of the first eye 1-1 and the second eye 1-2 of a patient at an apparent distance, and a determining 140 of an accommodative convergence of the first eye 1-1 and the second eye 1-2 at the apparent distance using the measured disassociated phoria. As mentioned earlier, the method 100 is a two-stage method, and thus its results integrate the information and knowledge revealed by the two different stages.

As described below in detail, in some embodiments, the measuring 120 can include projecting non-fusible visible images 26-1 and 26-2 for the first eye 1-1 and the second eye 1-2 using the stereo display 20 of the system 10. For the purpose of describing the method 100 more concisely, the visible images 26-1 and 26-1 of FIGS. 5-10 will be simply referred to as images 26-1 and 26-2 in what follows.

Figure 1A:
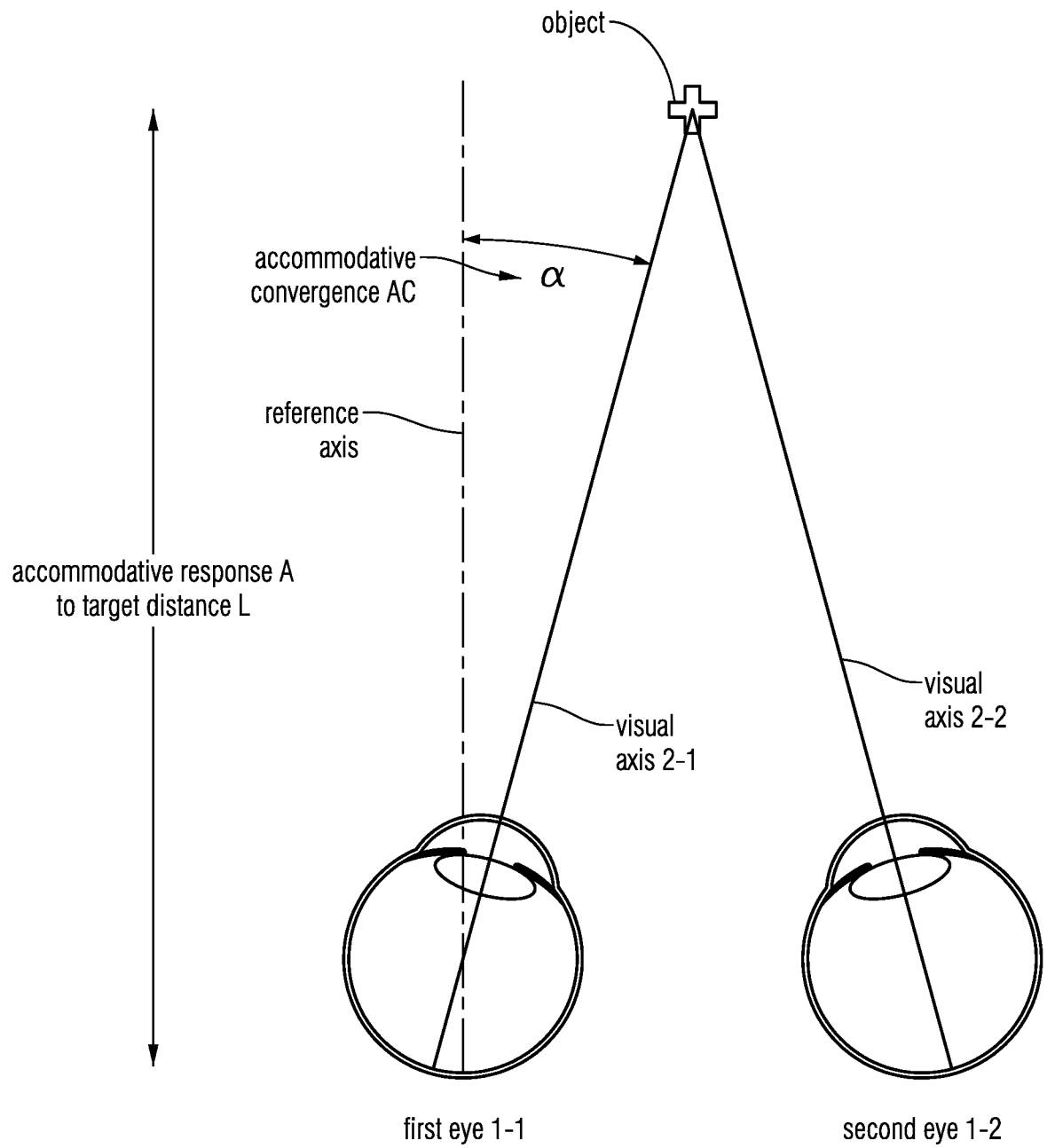
FIGS. 1A-C illustrates various accommodative misalignments.
Figure 1B:
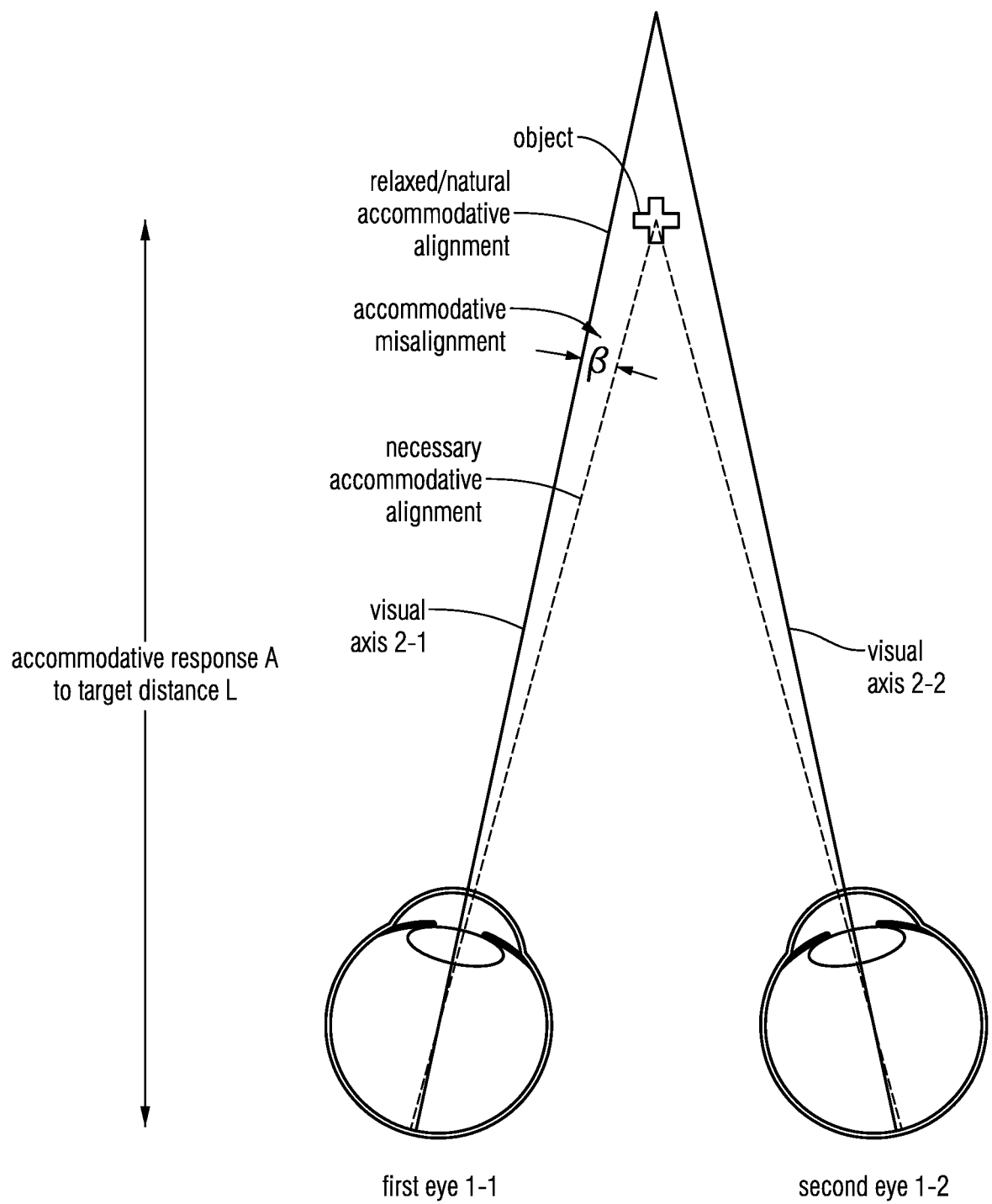
Figure 1C:
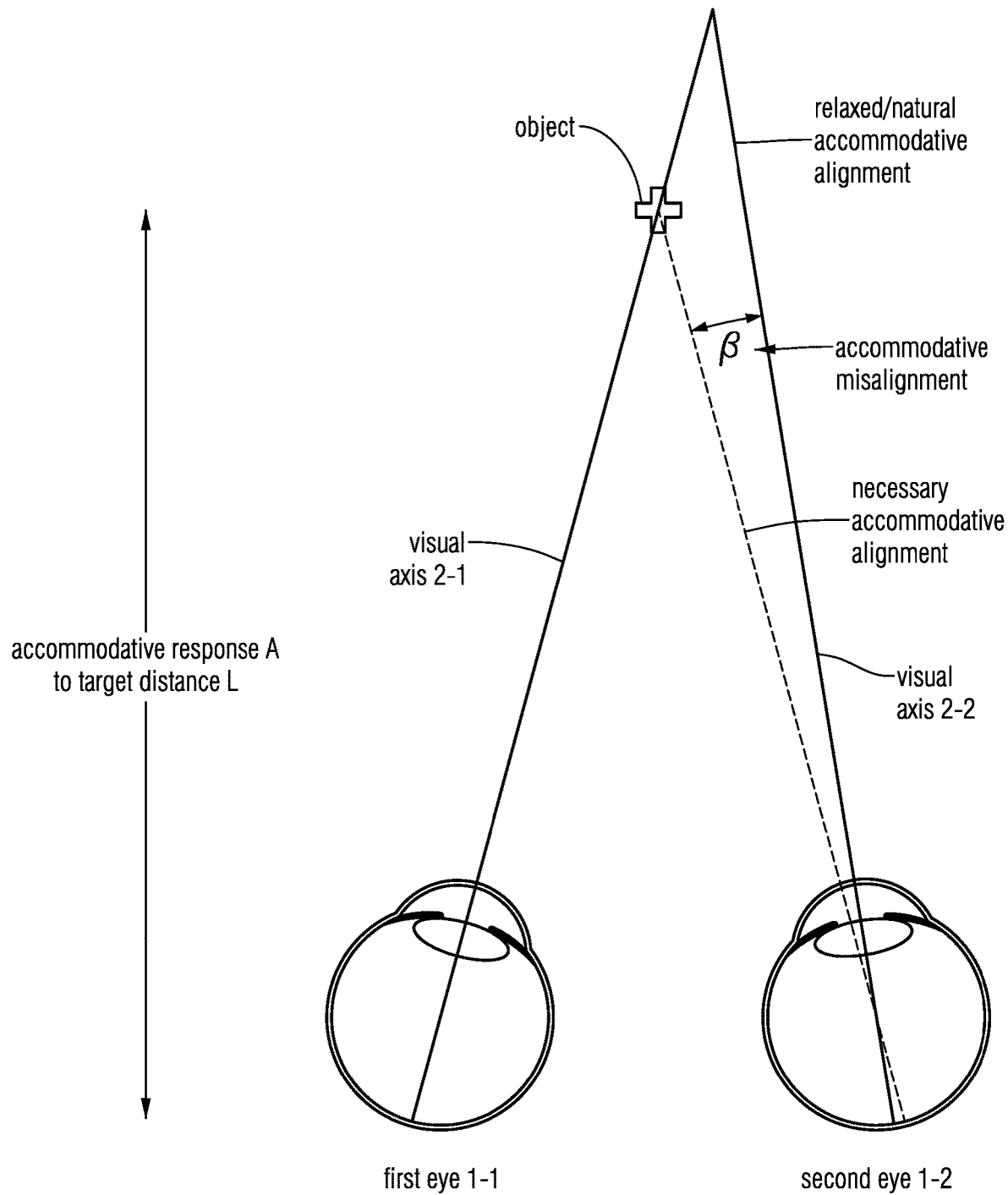
Figure 2A:
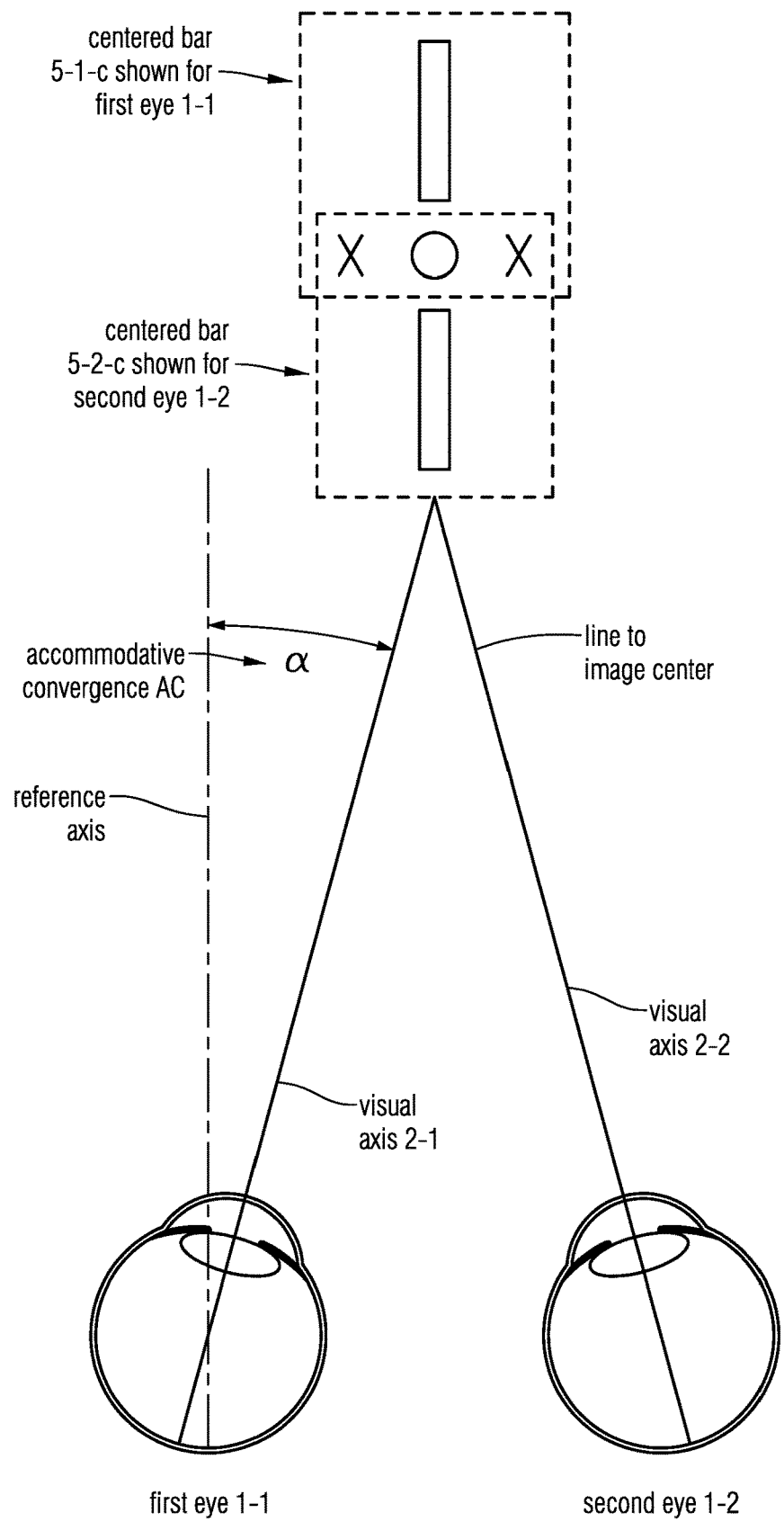
FIGS. 2A-D illustrate method to determine types of accommodative misalignments.
Figure 2B:
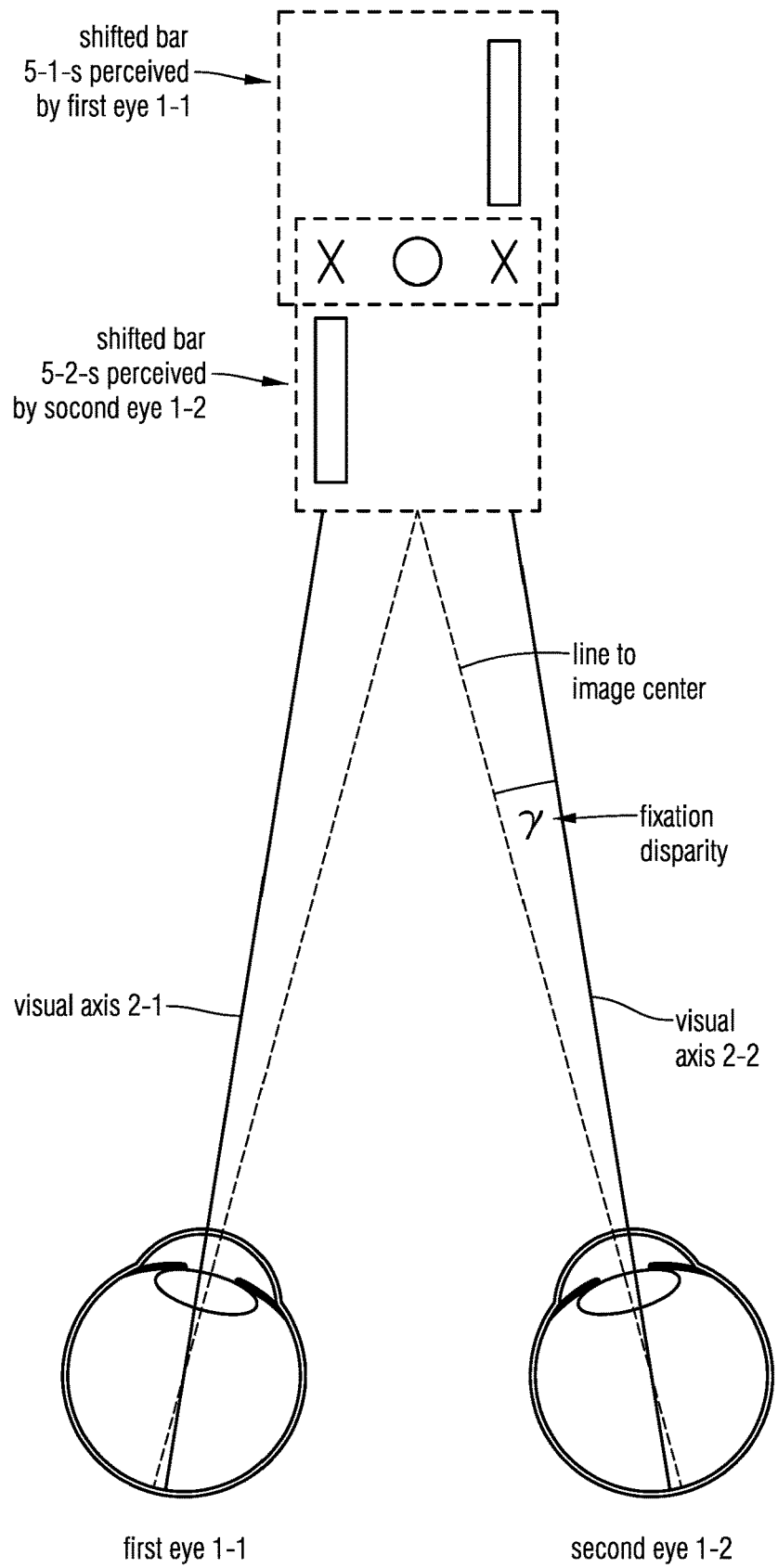
Figure 2C:
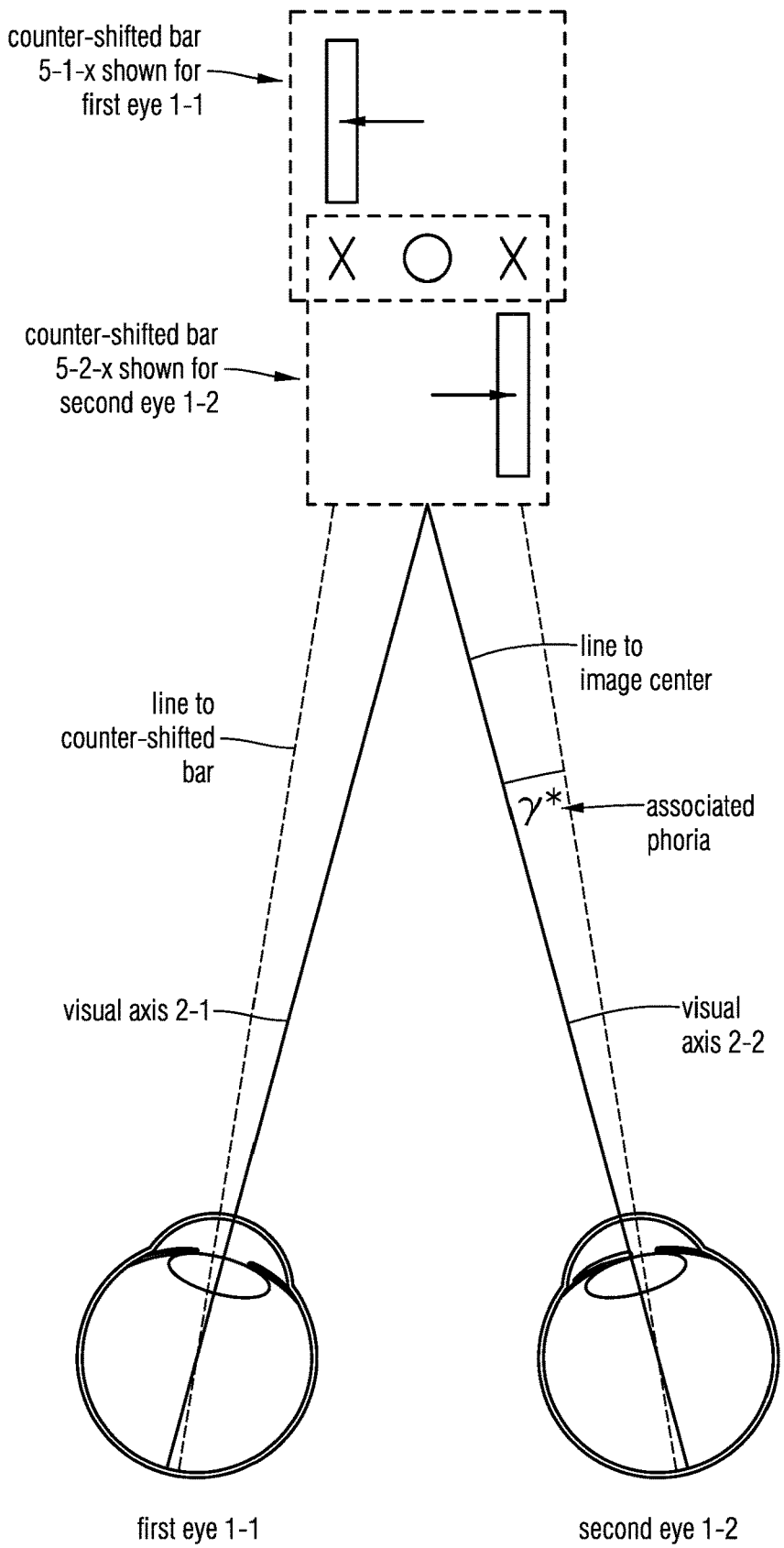
Figure 2D:
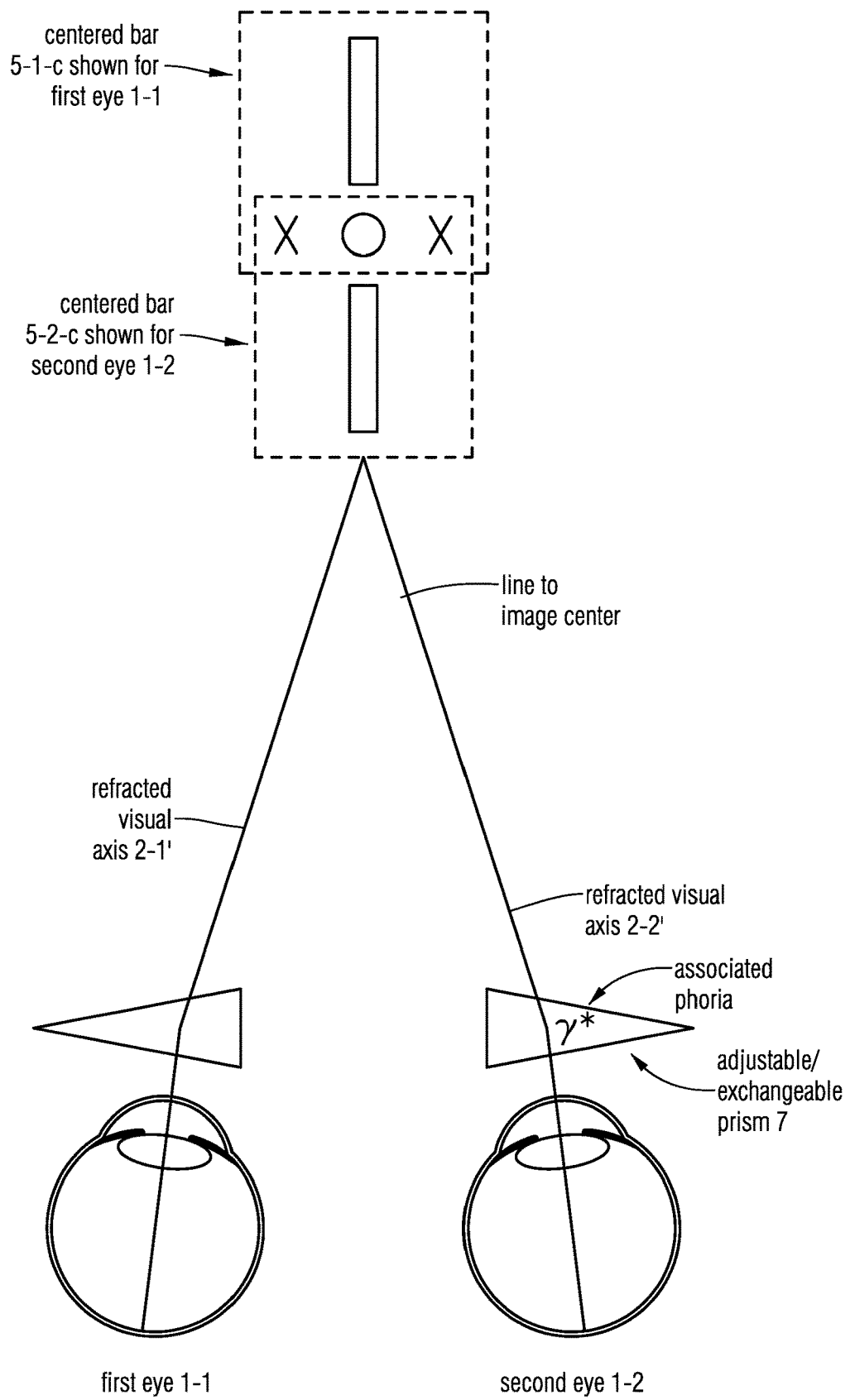

Examples of projecting non-fusible images in order to determine a disassociated phoria have been described, e.g., in relation to FIGS. 2C-D. There, the two non-fusible images 6-1-*s* and 6-2-*s* were of comparable appearance, or dominance. Some embodiments of the method 100 also involve projecting such non-fusible images of comparable dominance.

In other embodiments, the projecting can include projecting a dominant image for the first eye 1-1, and projecting a non-dominant image for the second eye 1-2. As described in relation to FIGS. 2C-D, the eye 1-2 that sees the non-dominant image often starts wandering off after the brain's efforts to fuse the two non-fusible images fail. In these embodiments, the measuring 120 can include tracking the eyes 1-1 and 1-2 with the eye tracker 40, and determining when the wandering eye 1-2 eventually achieves a relaxed orientation. Achieving this relaxed state can be inferred, for example, by the eye tracker 40 determining that the movement of the eye 1-2 slowed below a threshold, or changed from a directional movement to a random jitter, or came to a halt. Once the eye tracker 40 determined that the eye 1-2 reached the relaxed state, the disassociated phoria can be measured by measuring an orientation of at least one of the first eye 1-1 and the second eye 1-2 by the eye tracker 40.

Figure 12:
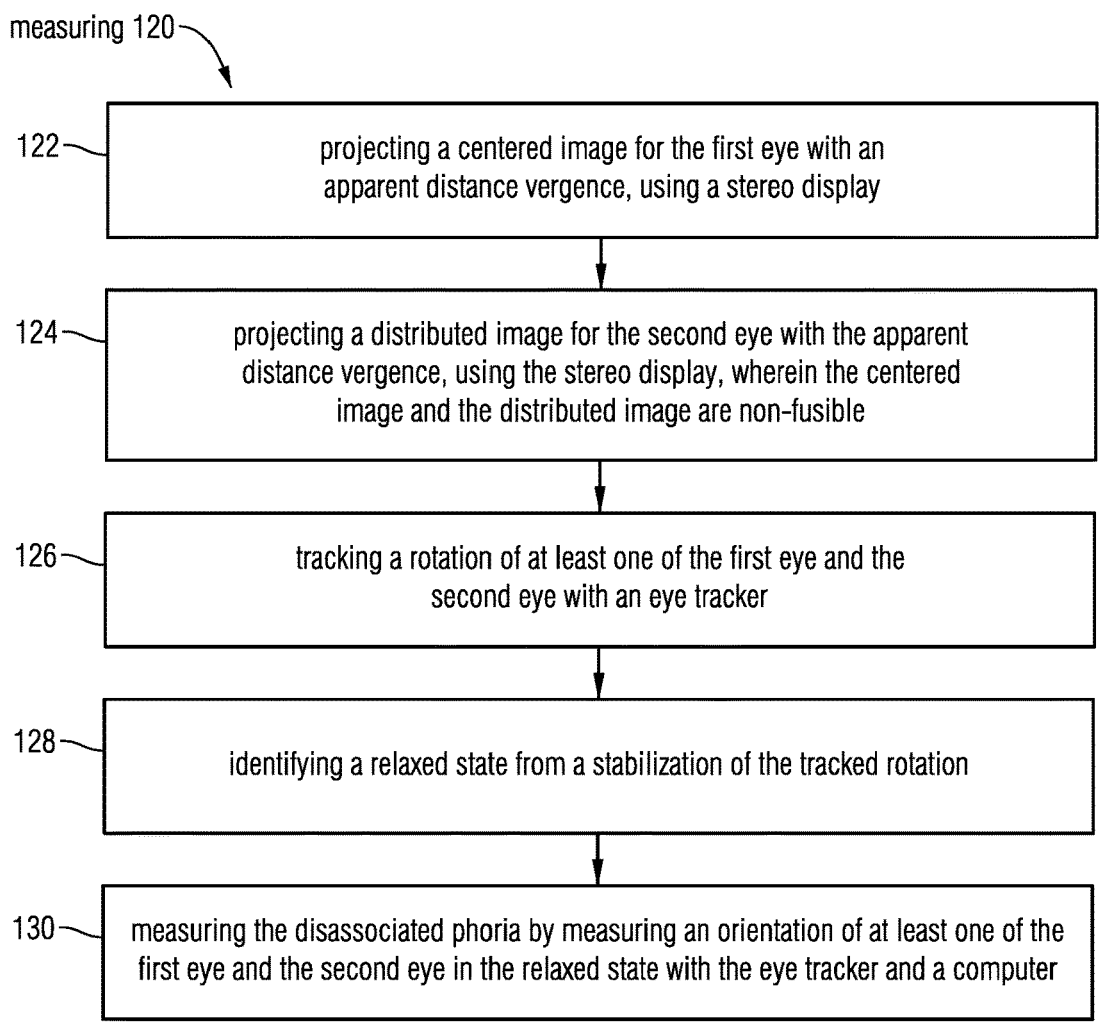
FIG. 12 illustrates exemplary details of the measuring step.

FIG. 12 describes implementations of these steps in more detail, and FIGS. 13A-D illustrate these steps in a particular embodiment. In these embodiments, the measuring 120 can include the followings.

Projecting 122 a centered image for the first eye with an apparent distance vergence, using a stereo display;

projecting 124 a distributed image for the second eye with an apparent distance vergence, using the stereo display, wherein the centered image and the distributed image are non-fusible;

tracking 126 a rotation of at least one of the first eye and the second eye using an eye tracker;

identifying 128 a relaxed state from a stabilization of the tracked rotation; and measuring 130 the disassociated phoria by measuring an orientation of at least one of the first eye and the second eye in the relaxed state using the eye tracker and a computer.

Figure 13A:
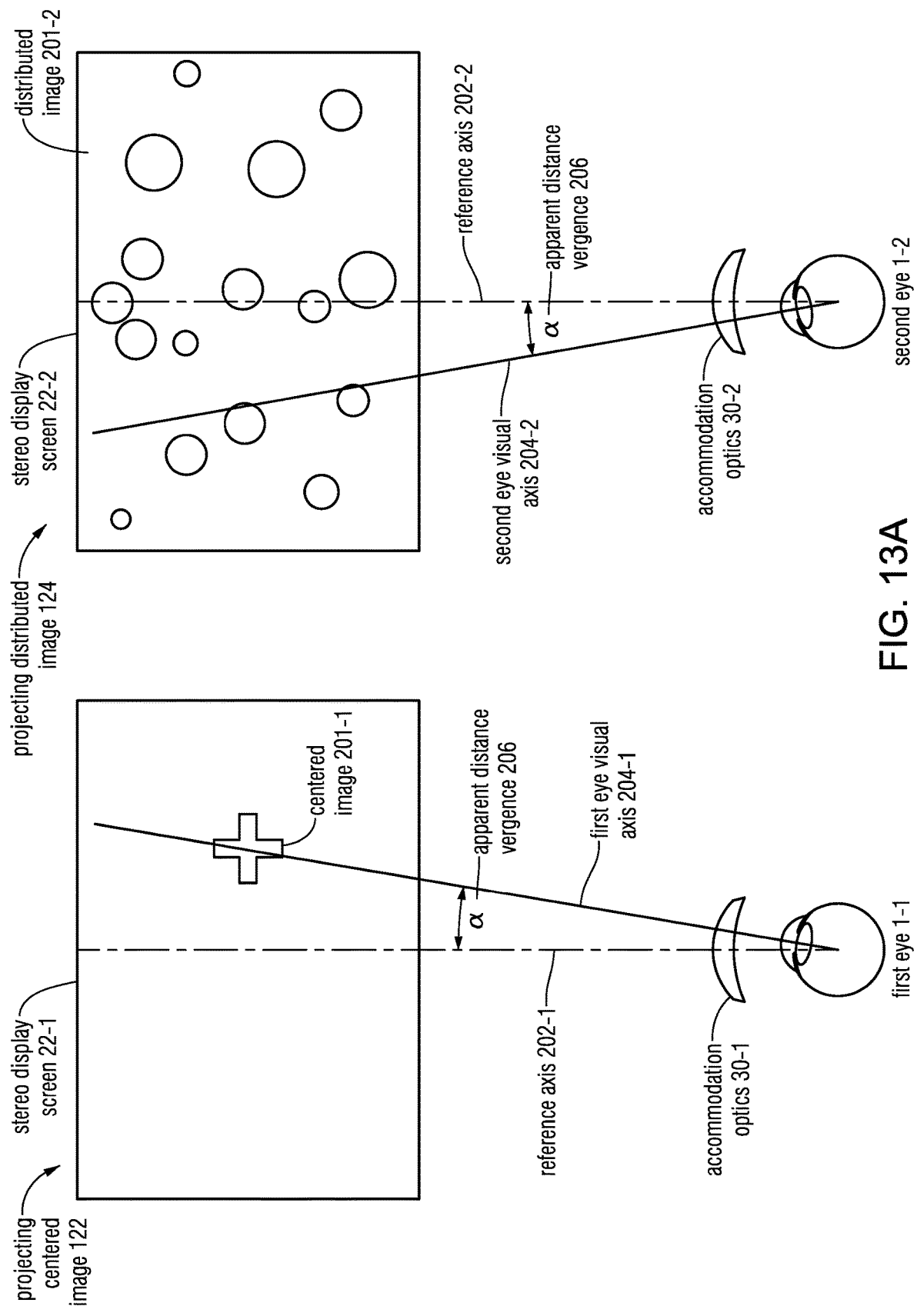
FIGS. 13A-D illustrate steps of carrying out the measuring step.

FIG. 13A, left panel illustrates that the projecting of a centered image step 122 can include projecting a centered image 201-1, a cross in this case, on the stereo display screen 22-1 of the stereo display 20 of the system 10. The projecting 122 can be done with an apparent distance vergence 206. A reference axis 202-1 is introduced for reference as a central normal that connects a center of the first eye 1-1 with a center of the stereo display screen 22-1. With this, the apparent distance vergence 206 can be characterized by an apparent distance vergence angle $\alpha=\alpha(L)$, the angle that a first eye visual axis 204-1 makes with the reference axis 202-1 when looking at an object that is placed halfway between the two eyes 1-1 and 1-2 at the apparent distance L. More generally, the apparent distance vergence 206 will be represented by and referred to as the line directed from a center of the first eye 1-1 with the angle $\alpha(L)$ relative to the reference axis 202-1, even if the first eye visual axis 204-1 is not pointing along this line.

The centered image 201-1 is centered in the sense that it is moved off the center of the stereo display screen 22-1 only by the apparent distance vergence angle α(L) to simulate the apparent distance vergence 206. For brevity's sake, sometimes this angle will be only referred to as the vergence angle α. The definition of the first eye visual axis 204-1 can incorporate a lens or any other relevant portion of the accommodation optics 30-1, through which the first eye 1-1 is observing the centered image 201-1.

Figures 4A, 4B:
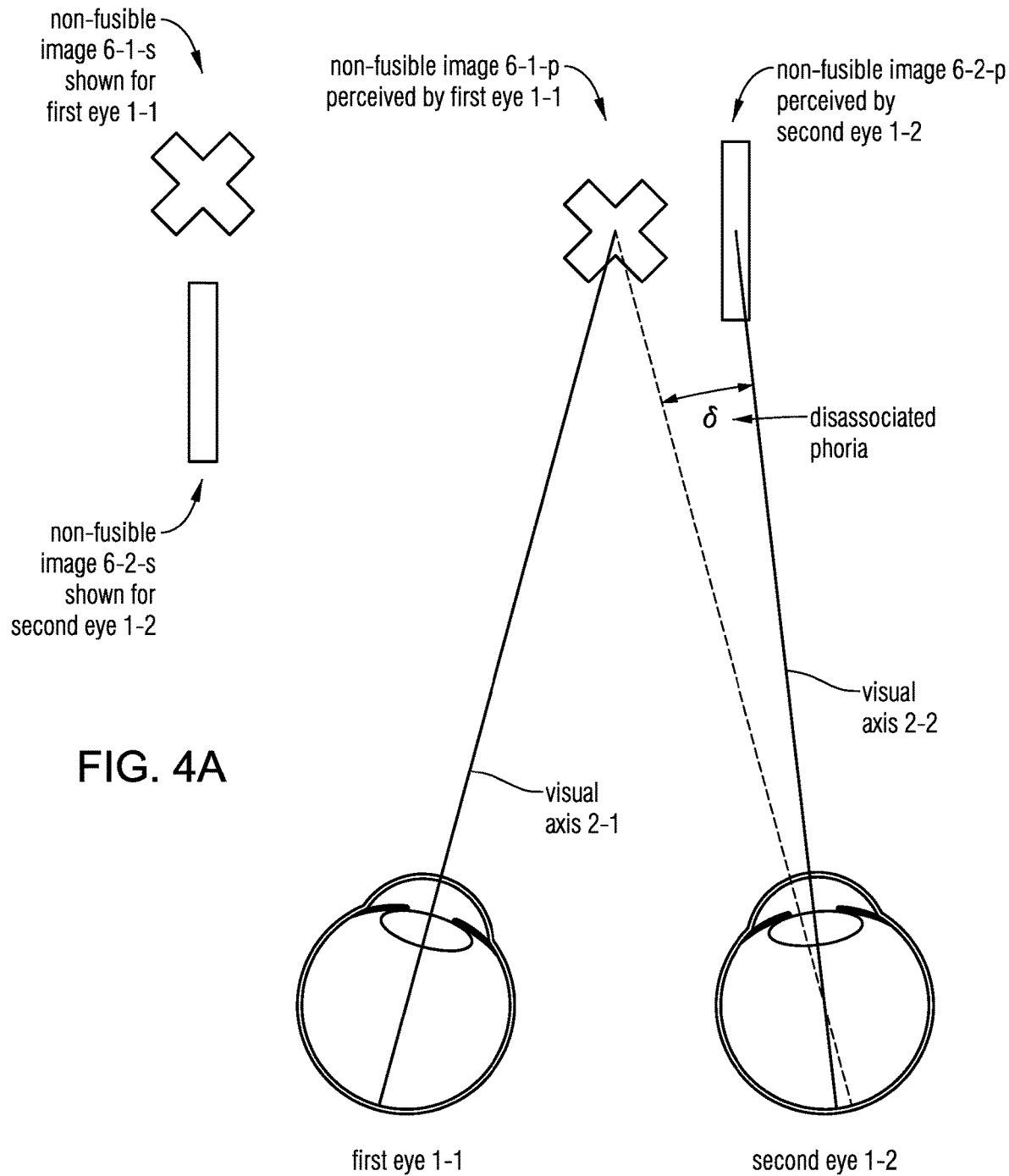
FIGS. 4A-C illustrate methods to determine disassociated phoria.
Figure 4C:
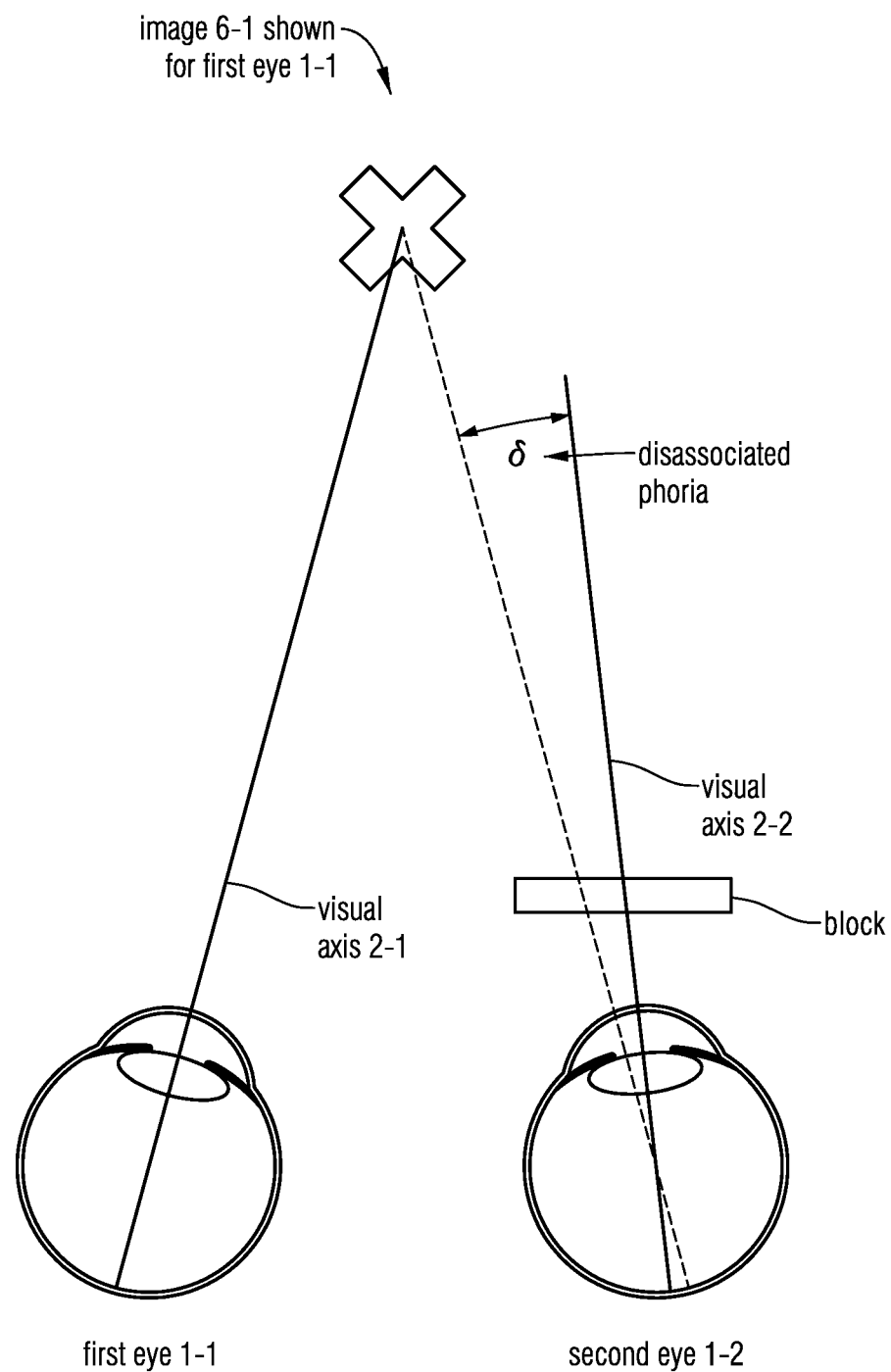

FIG. 13A, right panel illustrates the projecting of a distributed image step 124 for the second eye 1-2, in this case, a set of irregularly placed balls or spheres of random size and position, without an apparent center. The centered image 201-1 is an example of a dominant image, and the distributed image 201-2 is an example of a non-dominant image. The centered, dominant image 201-1 and the distributed, non-dominant image 201-2 are examples of non-fusible images. Alternatively, the stereo display screen 22-2 can be simply darkened as another embodiment of the non-fusible distributed image 201-2, instead of the irregularly placed balls, in analogy to the block in FIG. 4C.

Figure 13B:
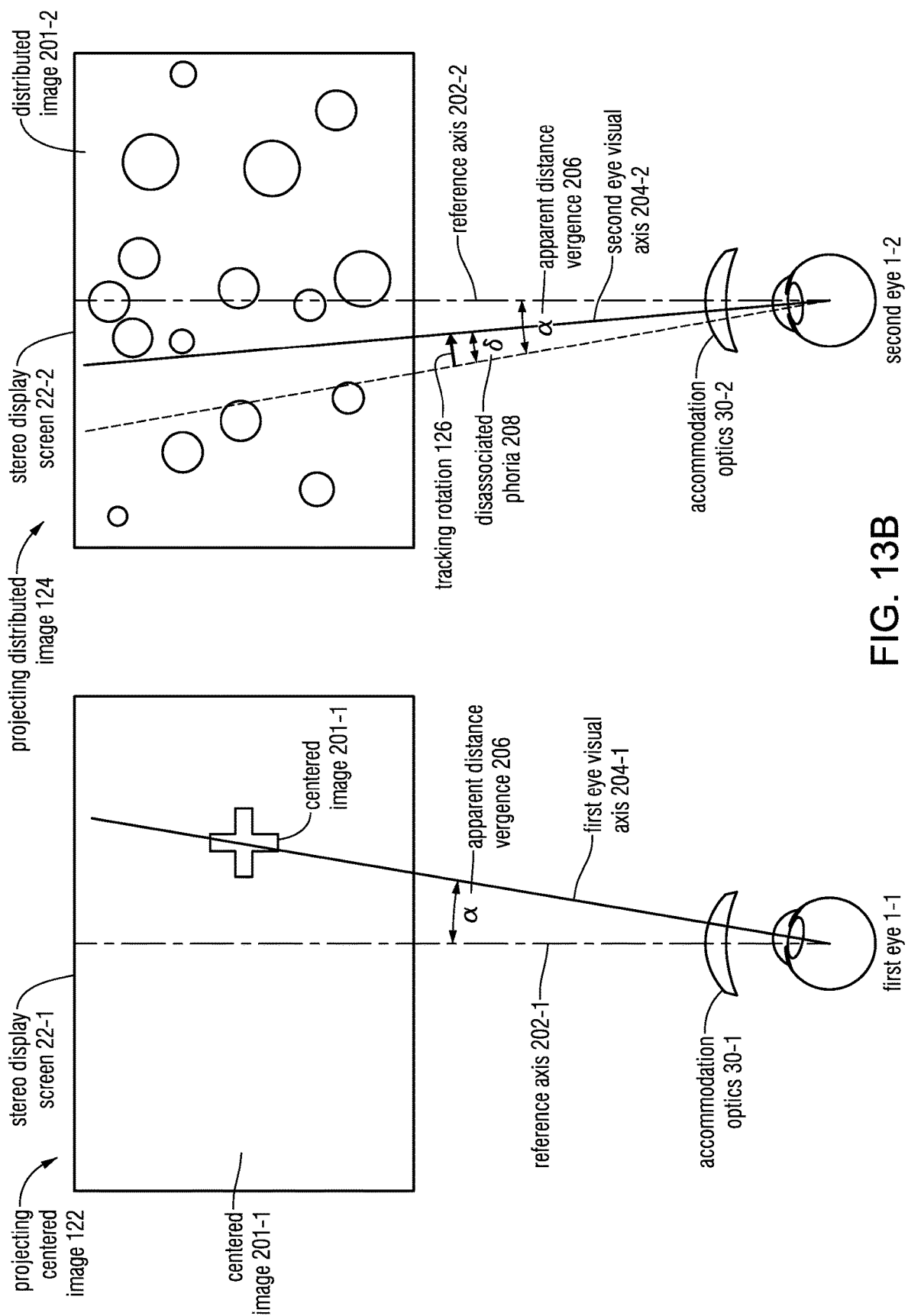

FIG. 13B illustrates that, as described earlier, the second eye 1-2 will initially also turn inward by approximately the same apparent distance vergence angle α as the first eye 1-1, but, after the brain fails to fuse the non-fusible central image 201-1 and distributed image 201-2, the second eye 1-2 wanders away. The eye tracker 40 can execute the tracking step 126 of the second eye 1-2 until the optometrist, or an automated program, determines that the wandering second eye 1-2 reached a relaxed state from a stabilization of the tracked rotation in the identifying step 128. This stabilization can be defined in various ways: from the eye coming to a stop, or an amplitude of the eye's jitter becoming less than a threshold, or a directional rotation of the eye evolving into a directionless wandering.

In the measuring step 130, once the relaxed state has been identified in step 128, the eye tracker 40 can measure the orientation of the relaxed second eye 1-2 by determining the angle δ the second eye visual axis 204-2 with the apparent vergence 206. In this measuring step 130, δ, the angular deviation of the relaxed second eye 1-2 from the apparent distance vergence 206 will be referred to as the disassociated phoria 208, with its disassociated phoria angle δ. This definition is in close analogy with that of FIGS. 4B-C. As mentioned before, small differences exist among various practitioner's definitions of the disassociated phoria.

In some related embodiments, the tracking step 126 may involve tracking a rotation of the first eye 1-1, the second eye 1-2, or both. In these embodiments, the disassociated phoria 208 can be defined from measuring 130 a first eye phoria angle δ-1, a second eye phoria angle δ-2, and determining the disassociated phoria δ as some type of a mean of δ-1 and δ-2.

FIGS. 13A-B illustrated that the steps 122-130 of the overall measuring step 120 can be performed as a near vision distance, e.g. L being in the range of 40 cm-100 cm.

Figure 13C:
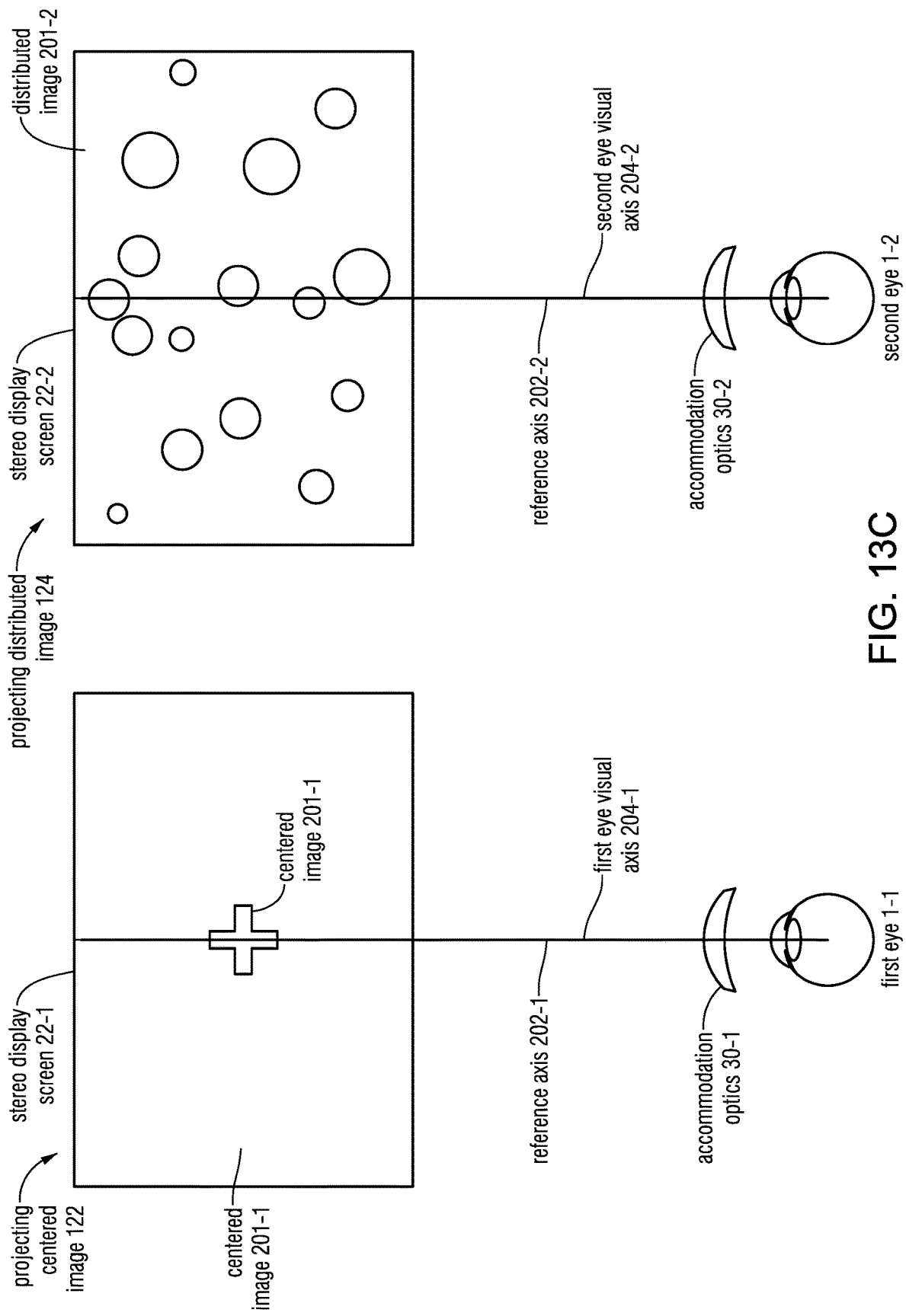
Figure 13D:
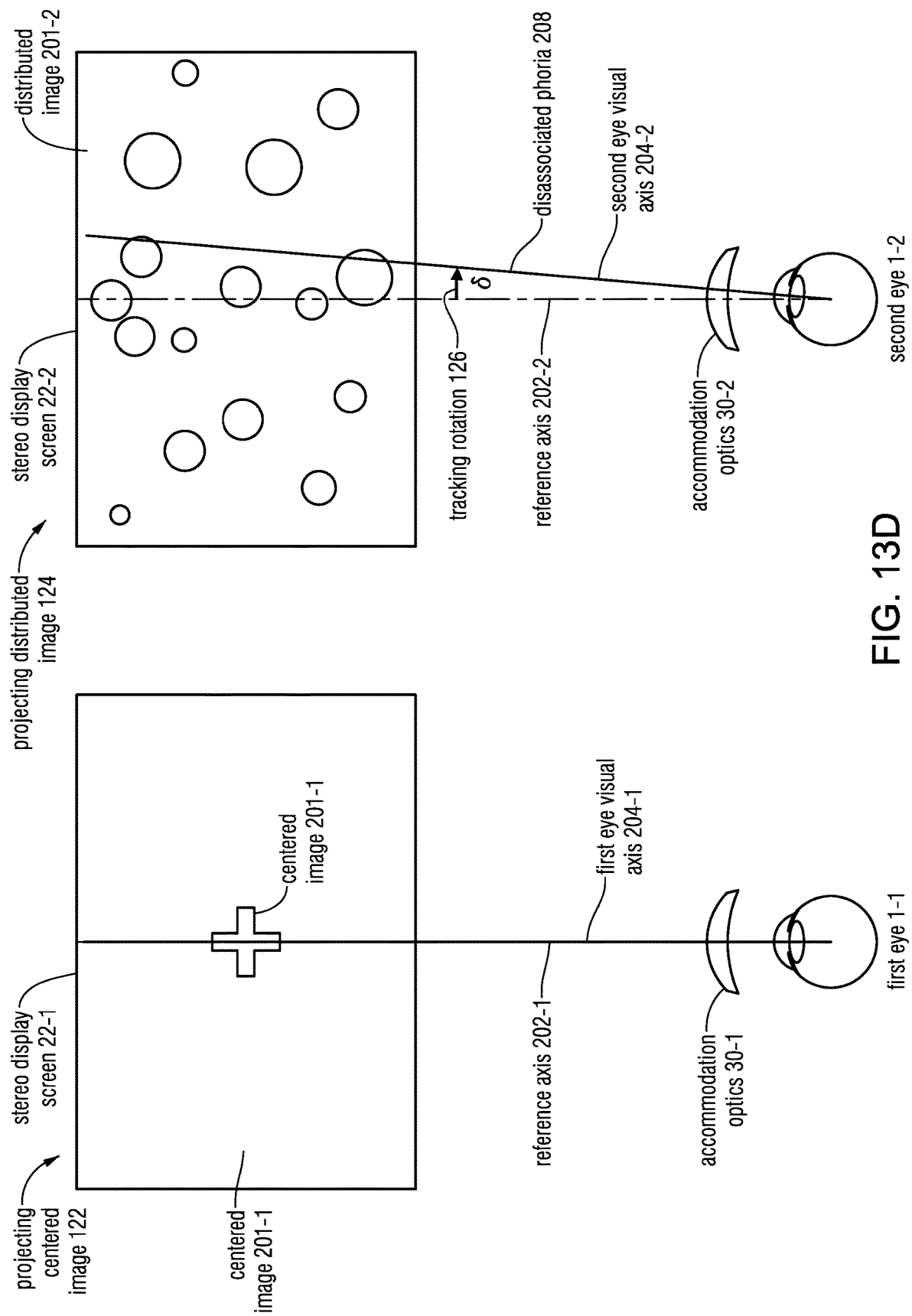

FIGS. 13C-D illustrate that the same steps 122-130 can be also performed as part of a distance vision test, when the apparent distance is L large, and the apparent distance vergence angle is α=0. In related embodiments, L can be in the 1 m-10 m range. Expressed in diopters, the method 100 can be performed at near vision distances corresponding to 1-3D, at distance vision distances corresponding to 0-0.5D.

To summarize, the result of the measuring step 120, the first stage of the method 100, is the disassociated phoria 208, with its disassociated phoria angle δ. The second stage of the method 100, the determining step 140, carries out additional tests of the prismatic misalignment that build on the just determined disassociated phoria 208. Therefore, the overall method 100 is a combination of the first and second stages and thus the method 100 integrates two distinct tests of prismatic misalignments, and thus integrates knowledge and data about two different types of the binocular alignment. Doing so promises a qualitatively more complete treatment and a qualitatively better improvement of the visual acuity.

Figure 14:
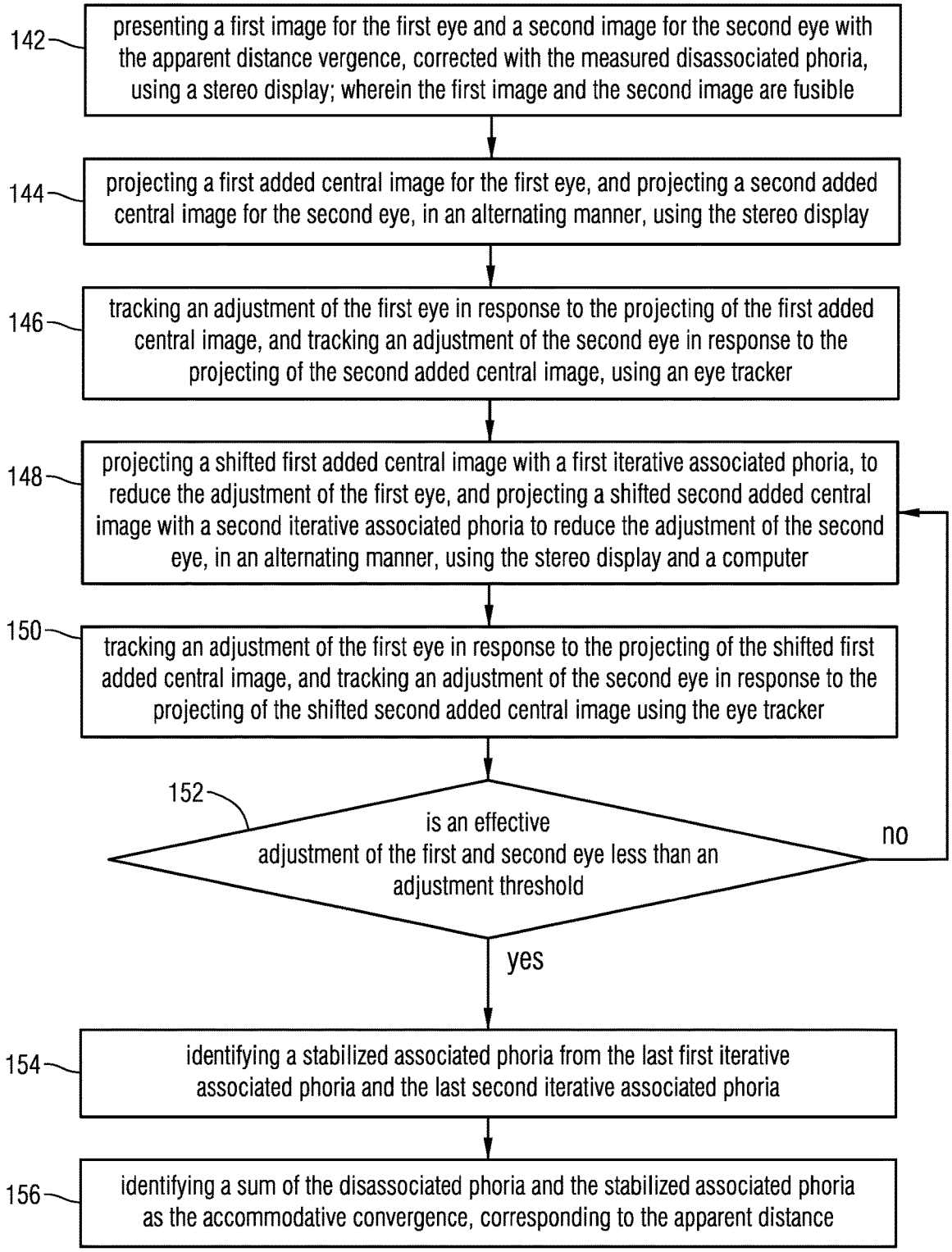
FIG. 14 illustrates exemplary details of the determining step.

FIG. 14 illustrates that the determining step 140 can include a presenting step 142 of a first image for the first eye and a second image for the second eye, with the apparent distance vergence, corrected with the measured disassociated phoria, using the stereo display; wherein the first image and the second image are fusible.

Figure 15A:
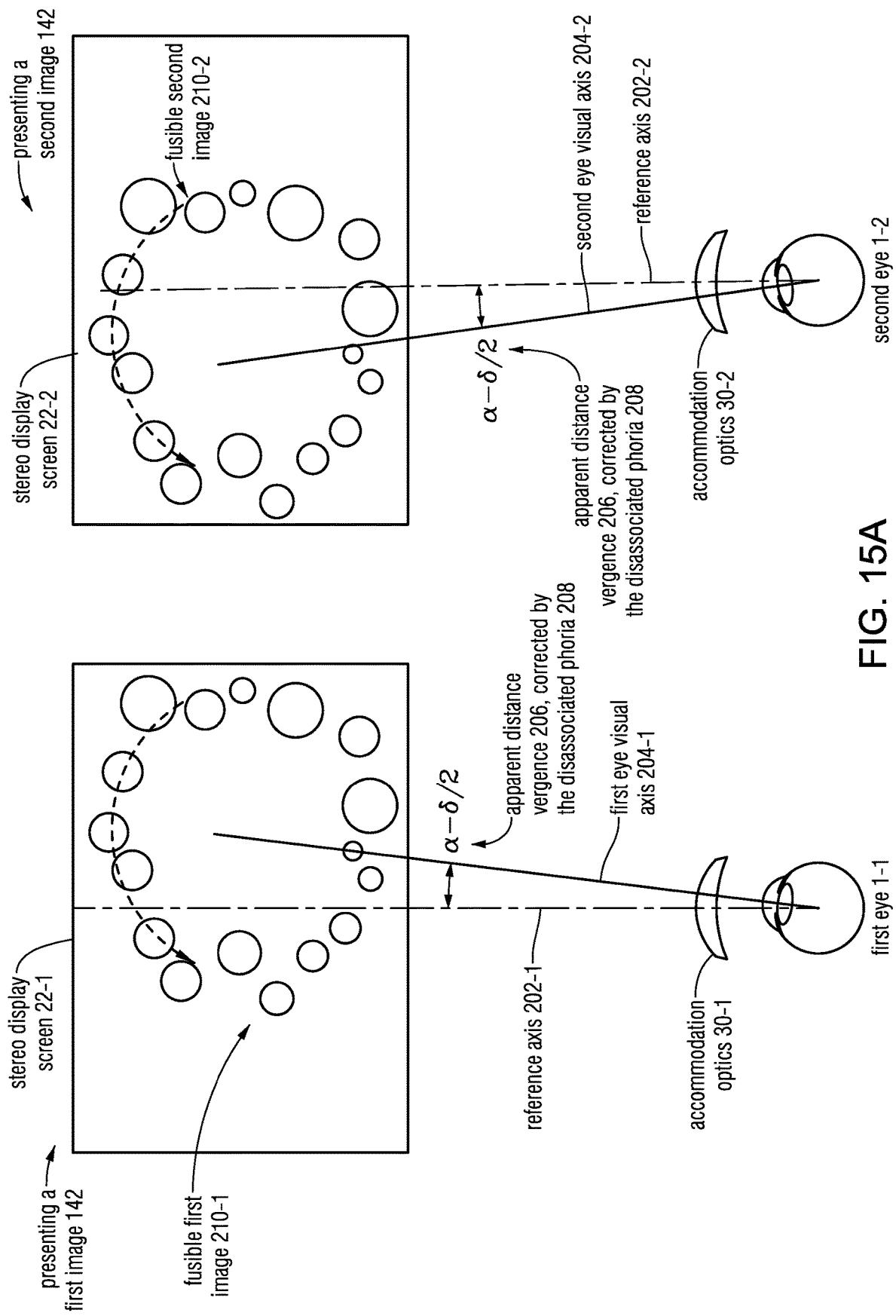
FIGS. 15A-C illustrate steps of carrying out the determining step.

FIG. 15A illustrates that in some implementations of the presenting step 142, a fusible first image 210-1 can be presented on the stereo display screen 22-1 for the first eye 1-1, and a fusible second image 210-2 can be presented on the stereo display screen 22-2 for the second eye 1-2. These fusible images 210-1 and 210-2 can be peripheral. For example, the peripheral images 210-1 and 210-2 can be two, essentially identical circular bands, or rings, of balls or planets, as shown. Centers of the fusible images 210-1 and 210-2 can be shifted towards each other according to the apparent distance vergence 206, the vergence angle α being corrected by the disassociated phoria δ (208), as measured in the measuring step 120. The measured disassociated phoria δ can be symmetrically distributed as δ/2-δ/2 between the two eyes, as shown. In these typical cases, the centers of the fusible images 210-1 and 210-2 can be shifted towards each other according to α-δ/2, the vergence angle α, corrected by the disassociated phoria δ, relative to the reference axes 202-1 and 202-2. In response, the first eye visual axis 204-1 and the second eye visual axis 204-2 typically align with the apparent distance vergence 206, corrected by the disassociated phoria 208, as shown by these visual axes 204 pointing towards the centers of the fusible images 210.

In some cases, when the binocular misalignment of the two eyes is asymmetric, the optometrist may have reasons to attribute the measured disassociated phoria δ unevenly between the two eyes. It is also noted that the earlier convention is continued to make the description more comprehensible: the description will refer to a pair of "limitation N-1 and limitation N-2" simply as "limitations N", where doing so does not lead to confusion.

The shift of the fusible images 210 can be impacted by the accommodation optics 30. The settings of the accommodation optics 30 can depend on L, the accommodative distance, or a spectacle power preferred by the patient, possibly further corrected by a cylinder or aberration.

In some embodiments, the fusible first image 210-1 and the fusible second image 210-2 can be dynamic. In FIG. 15A, the directed dashed arcs indicate that the rings of planets can be rotating around their center. Experiments have shown that making the peripheral fusible images 210 rotate captures peripheral prismatic effects more reliably and reproducibly. In the presenting step 142 the radius, spatial distribution, coloring, dynamics, and speed of rotation of these fusible images 210 could all be adjusted to provide the alignment information with the optimal weight.

In some embodiments, the first image 210-1 and the second image 210-2 can be static. In some embodiments, the first image 210-1 and the second image 210-2 can be central. These embodiments may present their own medical advantages.

Figure 15B:
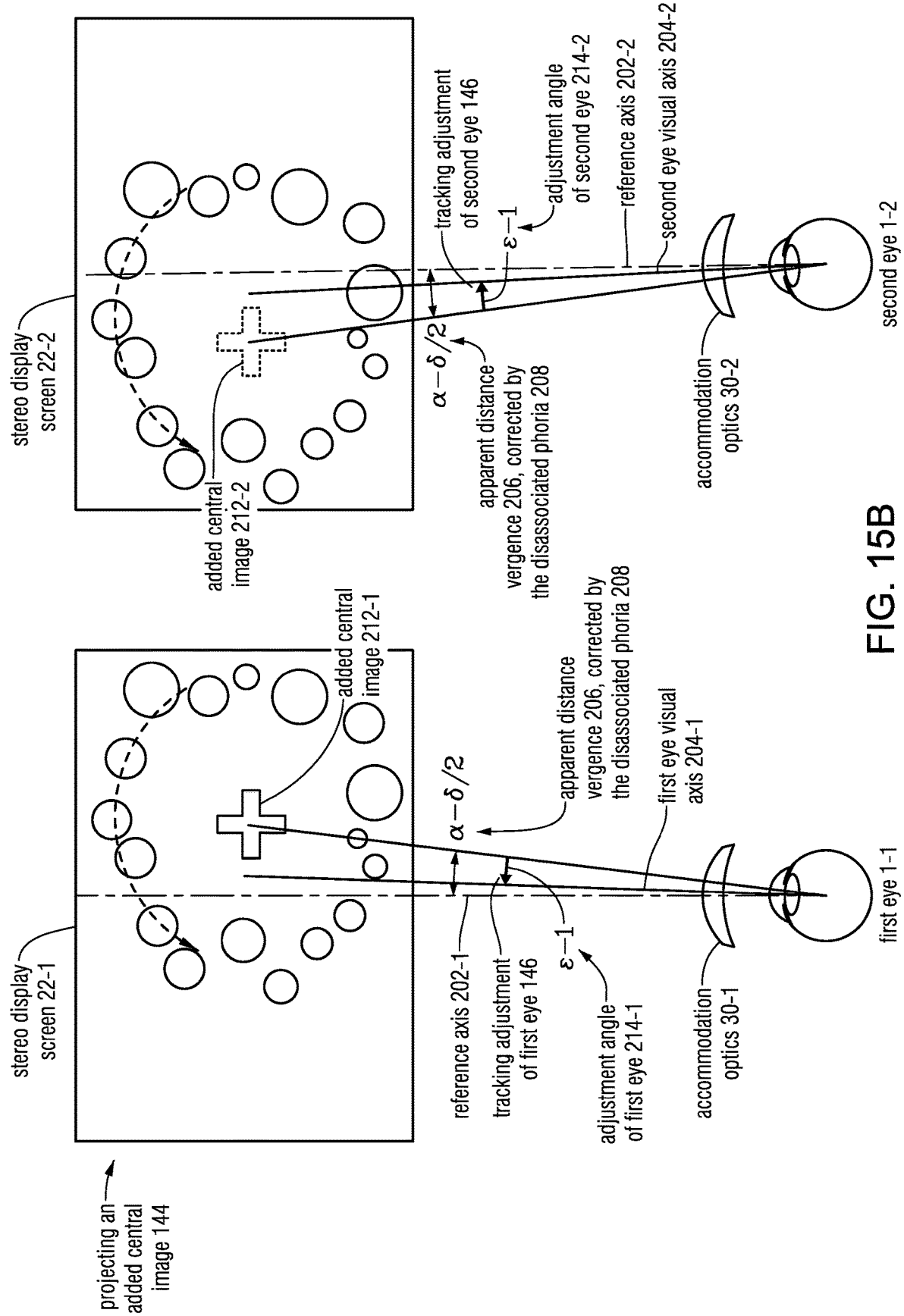

FIG. 14 describes and FIG. 15B illustrates that the presenting step 142 can be followed by a projecting step 144. The projecting step 144 can include a projecting of a first added central image 212-1 for the first eye 1-1, and a projecting a second added central image 212-2 for the second eye 1-2. These central images 212 can be projected at the center of the fusible images 210. In the embodiment of fusible images 210 being circulating planets, the added central images 212 can be projected at the center of their circulation, e.g., as a cross, as shown.

The projecting 144 of these two added central images 212-1 and 212-2 can be performed in an alternating manner, using the stereo display 20. To express the alternating manner of the projecting 144, only one of the added central images, the cross 212-1 is shown with a solid line, and the other added central image, 212-2 is shown with a dashed line in FIG. 15B. The period of the alternating can be selected according to several different criteria, and can be less than 1 second, in a range of 1-100 second, in some cases in a range of 5-10 seconds.

Had $\delta$, the angle of the disassociated phoria 208, measured in step 120, completely captured the binocular alignments of the eyes 1, then the eyes 1 would not have needed to adjust to the projecting step 144 of the added central images 212 with the vergence angle $\alpha$, corrected by the disassociated phoria angle $\delta/2$. This would have manifested itself in that the eye visual axes 204 would have had remained aligned with the vergence angle $\alpha$, corrected by the disassociated phoria angle $\delta/2$ after the projecting step 144.

However, Applicant's studies revealed that patients moved and adjusted their eyes 1 in response to the projecting 144 of the added central images 212 with the corrected vergence angle $\alpha$-$\delta/2$. This led Applicant to the recognition that additional measurements were necessary to determine the remaining, residual prismatic misalignment of the eyes. These additional measurements are described in steps 146-154, as follows.

Tracking 146 an adjustment of the first eye in response to the projecting of the first added central image, and tracking an adjustment of the second eye in response to the projecting of the second added central image, using an eye tracker;

projecting 148 a shifted first added central image with a first iterative associated phoria, to reduce the adjustment of the first eye, and projecting a shifted second added central image with a second iterative associated phoria, to reduce the adjustment of the second eye, in an alternating manner, using the stereo display and a computer;

tracking 150 an adjustment of the first eye in response to the projecting of the shifted first added central image, and tracking an adjustment of the second eye in response to the projecting of the shifted second added central image using the eye tracker;

determining 152 whether an effective adjustment of the first and second eye is less than an adjustment threshold, and returning to the projecting the shifted first added central image step if the effective adjustment of the first and second eye is greater than the adjustment threshold;

identifying 154 a stabilized associated phoria from the last first iterative associated phoria and the last second iterative associated phoria, if the effective adjustment of the first and second eye is less than the adjustment threshold; and identifying 156 a sum of the disassociated phoria and the stabilized associated phoria as a correction to the accommodative convergence, corresponding to the apparent distance. These steps are described in some detail next.

FIG. 14 describes and FIG. 15B illustrates that in order to determine residual prismatic misalignments, the projecting step 144 can be followed by the tracking 146 of an adjustment of the first eye 1-1 in response to the projecting of the first added central image 212-1, and tracking an adjustment of the second eye 1-2 in response to the projecting of the second added central image 212-2, using an eye tracker 40. FIG. 15B illustrates that the first eye 1-1 adjusts to the projecting 144 by rotating the first eye visual axis 204-1 with an adjustment angle of the first eye 214-1, denoted by $\varepsilon$-1, and the second eye 1-2 adjusts by rotating the second eye visual axis 204-2 with an adjustment angle of the second eye 214-2, denoted by $\varepsilon$-2. From now on, for brevity, the angles will be referenced to the apparent distance vergence corrected by the disassociated phoria, having the angle $\alpha$-$\delta/2$, instead of the reference axis 202. The fact that the adjustment angles $\varepsilon$-1 and $\varepsilon$-2 were found non-zero, necessitated the subsequent steps of the determining step 140.

Figure 15C:
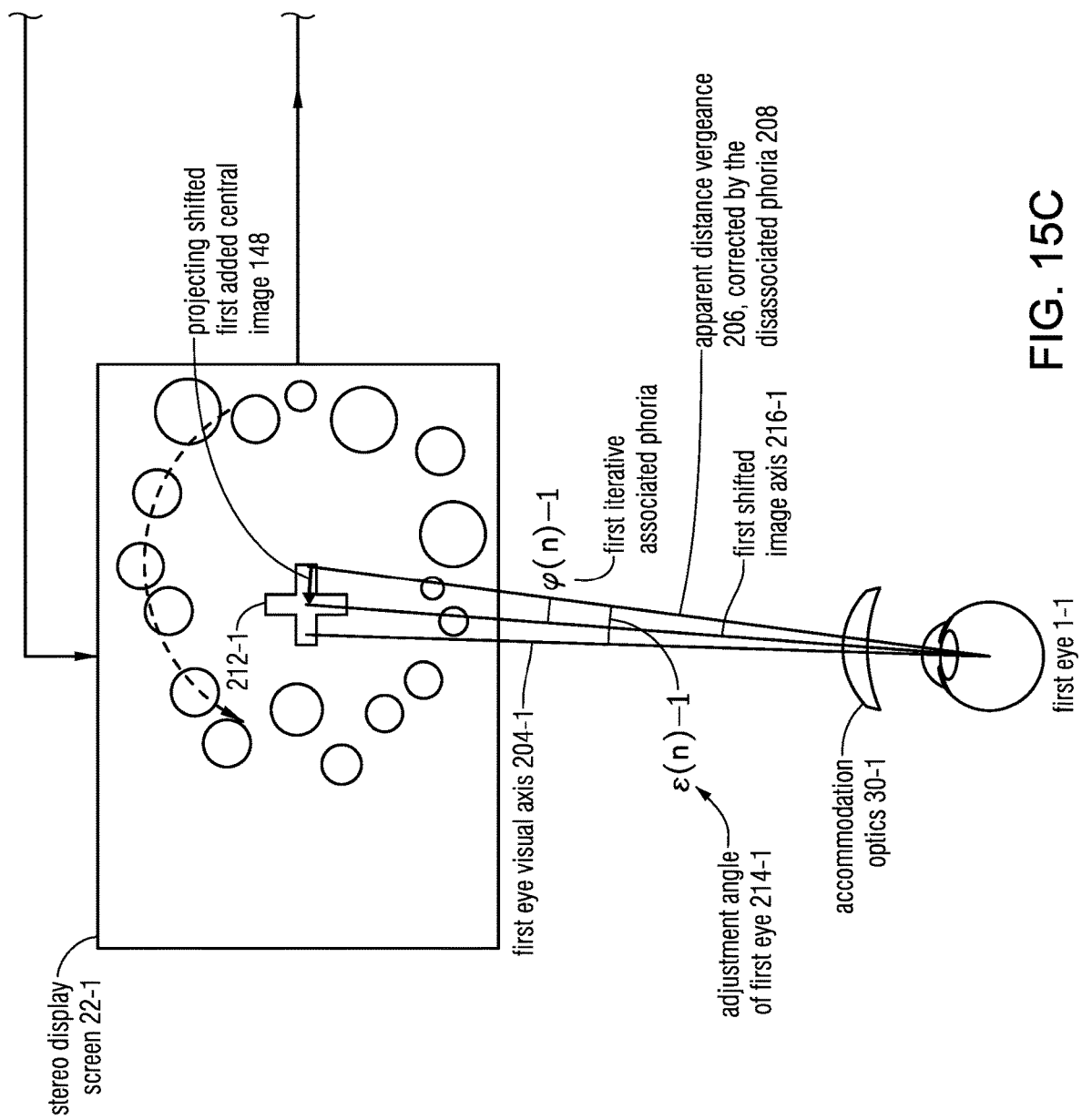
Figure 15C:
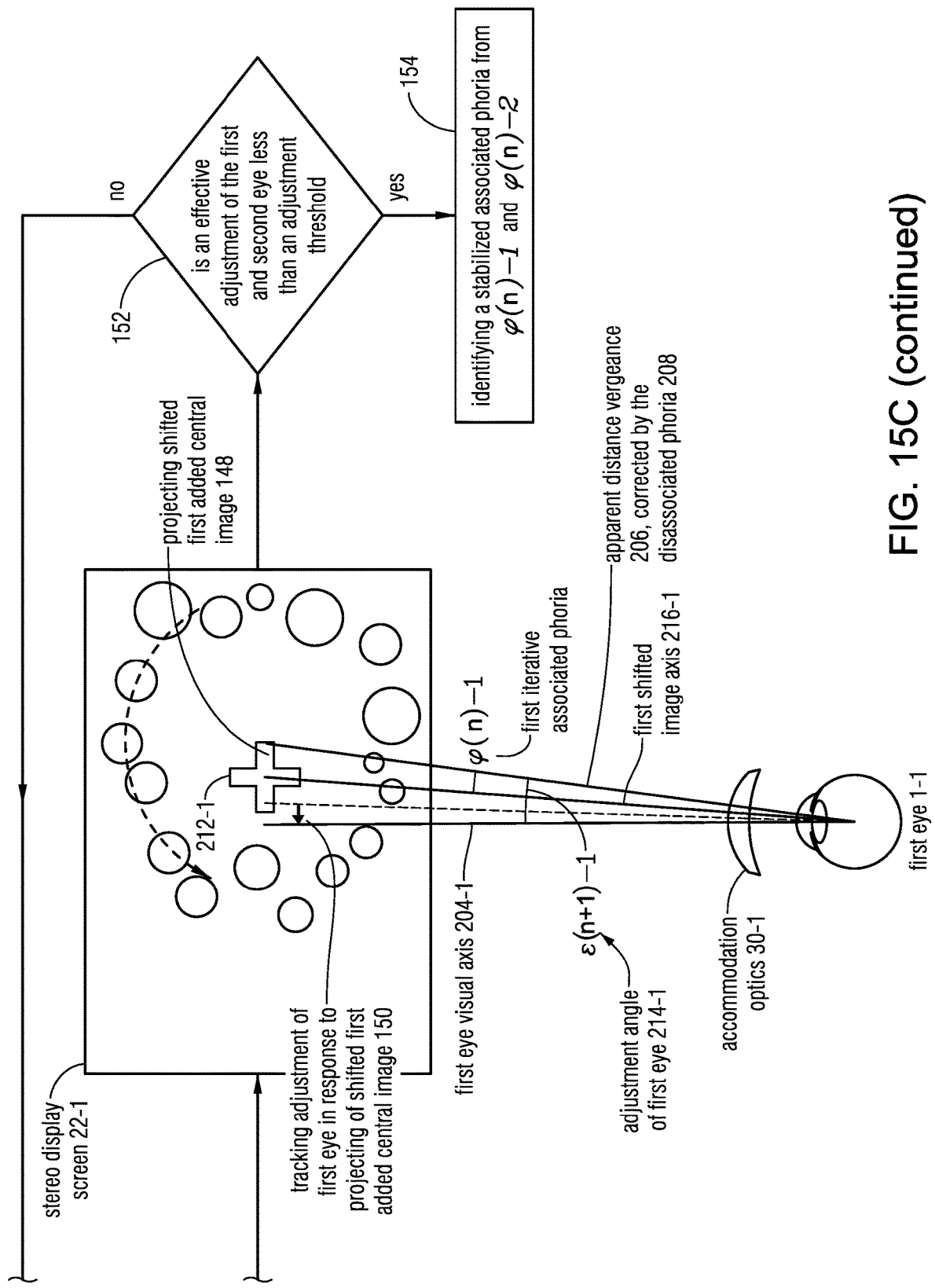

FIG. 15C shows that the determining the accommodative convergence step 140 next includes projecting 148 a shifted first added central image 212-1 with a first iterative associated phoria $\varphi(n)$-1, to reduce the adjustment of the first eye 1-1, and projecting a shifted second added central image 212-2 with a second iterative associated phoria $\varphi(n)$-2, to reduce the adjustment of the second eye 1-2. Here the adjustment of the eye can be measured by a change of the adjustment angle $\varepsilon(n)$-1, as elaborated below.

For clarity and brevity, in this FIG. 15C only the first eye 1-1 is illustrated explicitly. The shifted added central images 212 are connected to the eyes 1 and characterized by shifted image axes 216. FIG. 15C shows the first shifted image axis 216-1, connecting the shifted first added central image 212-1 to the first eye 1-1.

Figure 3:
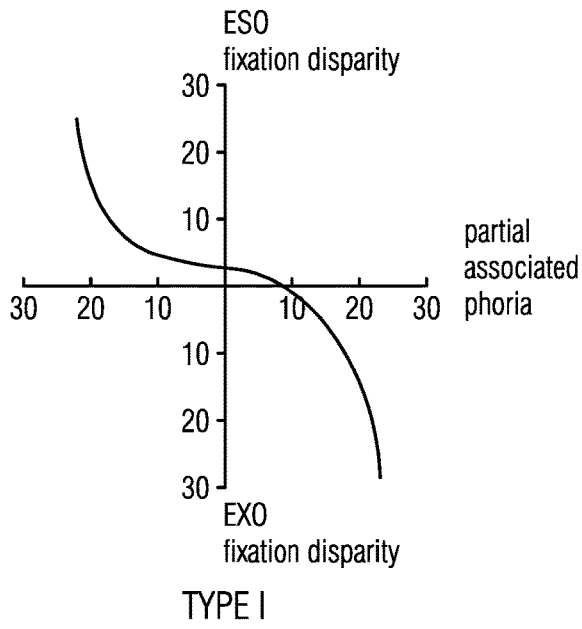
FIG. 3 illustrates four types of relationships between fixation disparity and partial associate phoria.
Figure 3:
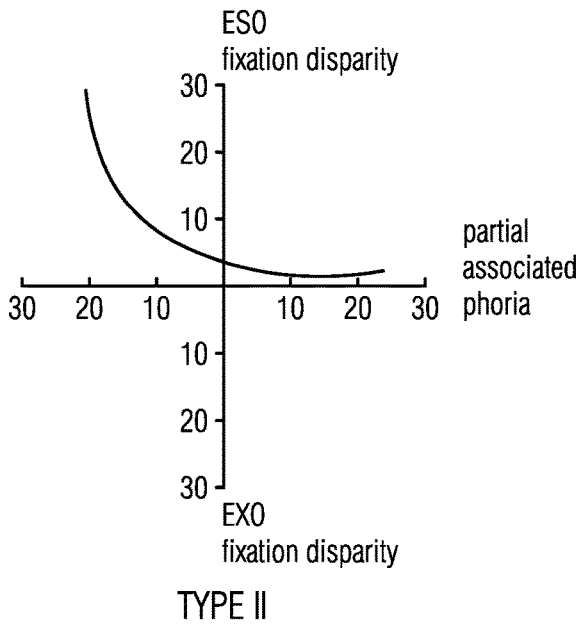
Figure 3:
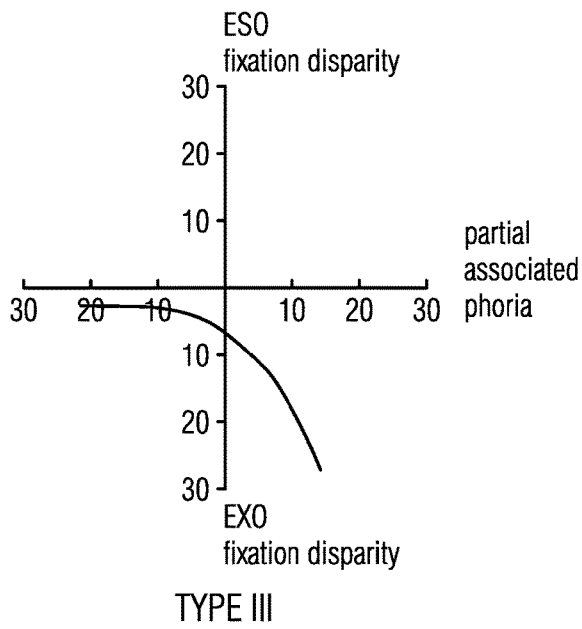
Figure 3:
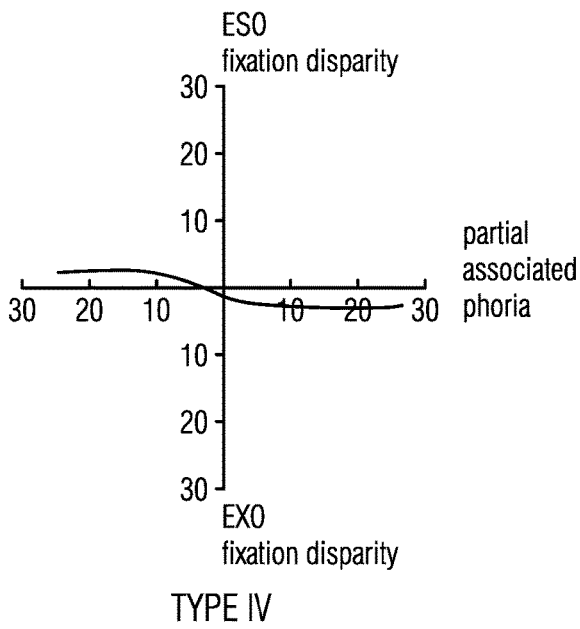

It was described in relation to FIGS. 2-3 that the fixation disparity $\gamma$ and the associated phoria $\gamma^*$, necessary to compensate it, are not simply equal and opposite to each other. In analogy to this recognition, the associated phoria $\varphi(n)$-1 is not simply equal and opposite to the adjustment angle of the first eye, $\varepsilon(n)$-1. Therefore, embodiments of the method 100 determine these quantities iteratively, in steps 1, 2, . . . n. The step index is shown in the above definitions as $\varphi(n)$-1 and $\varepsilon(n)$-1: the first first iterative associated phoria is denoted with $\varphi(1)$-1, the first second iterative associated phoria by $\varphi(1)$-2, and so on. Naturally, the "-1" and "-2" indices continue to label the angles of the first eye 1-1 and the second eye 1-2, respectively, while the "(1)", "(2)", . . . "(n)" indices label the first, second, and n-th steps of the iterative process.

As in the projecting step 144, the projecting 148 of these shifted added central images 212-1 and 212-2 can be performed in an alternating manner, using the stereo display 20 and the computer 50.

FIG. 15C further illustrates that the projecting step 148 can be followed by the tracking 150 of an adjustment of the first eye 1-1 in response to the projecting of the shifted first added central image 212-1, and tracking an adjustment of the second eye 1-2 in response to the projecting of the shifted second added central image 212-2, using the eye tracker 40. Specifying the presentation to the first eye 1-1 only, the tracking step 150 includes the tracking of the adjustment angle $\varepsilon(n+1)$-1 of the first eye 1-1 in response to the projecting 148 of the shifted first added central image 212-1 with the first iterative associated phoria φ(n)−1.

This tracking step 150 is analogous to the tracking step 146. It is distinguished by the iterative step index having grown from (n) to (n+1). In simplified terms, embodiments of the method involve shifting the added central image 212 with the iterative associated phoria φ(n), tracking the responsive adjustment angle ε(n+1) of the eye 1, determining the adjustment of the eye 1 from the change of the adjustment angle ε(n+1)−ε(n), and then repeating the shifting of the added central image 212 with a new iterative associated phoria φ(n+1), selected in magnitude and sign to reduce the change of the adjustment angle ε(n+1)−ε(n).

In some embodiments, the magnitude of φ(n+1)−φ(n) can be chosen to be equal to ε(n+1)−ε(n): |φ(n+1)−φ(n)|=|ε(n+1)−ε(n)|. In some cases, these embodiments may exhibit a slow convergence. Therefore, in some embodiments, |φ(n+1)−φ(n)| can be chosen to be equal to λ|ε(n+1)−ε(n)|: |φ(n+1)−φ(n)|=λ|ε(n+1)−ε(n)|, where λ<1. These embodiments often exhibit good convergence. Other, non-linear, polynomial, non-analytic or analytic relationships can also be employed in various embodiments.

After performing these steps 148 and 150 iteratively, the determining step 152 can be performed to determine whether an effective adjustment of the first and second eye is less than an adjustment threshold. Using the above framework, the determining step 152 may evaluate whether the change of the adjustment angle |ε(n+1)−ε(n)|, is less than a threshold. The effective adjustment can be defined in various ways. It can involve the change of the adjustment angle of only one of the eyes: |ε(n+1)−ε(n)| for the eye 1-1; or the sum of the changes of the adjustment angles for both eyes 1-1 and 1-2, or some weighted average, or a non-linear relation.

If the change of the adjustment angle |ε(n+1)−ε(n)| is greater than a threshold, then the method can return to the projecting step 148 of the shifted first added central image 212, as shown in FIG. 15C.

On the other hand, if in step (n), the adjustment of the eye, as characterized by, e.g., the change of the adjustment angle |ε(n)−ε(n−1)|, is found to be less than the threshold, then the iteration can stop and the method can continue with the identifying 154 of a stabilized associated phoria φ from the last first iterative associated phoria φ(n)−1, and the last second iterative associated phoria φ(n)−2. Again, different formulas can be adopted to define the stabilized associated phoria φ in this step 154, for example, φ=(φ(n)−1)+(φ(n)−2).

In the preceding embodiments, the disassociated phoria δ and the stabilized associated phoria φ were typically defined for the two eyes together. Thus, the per-eye values are half of the here-defined angles, in symmetrical cases.

The identifying step 154 can be followed by the identifying 156 of a sum of the disassociated phoria δ and the stabilized associated phoria φ, (δ+φ), as a correction to the accommodative convergence AC, with the accommodative convergence angle α, that corresponds to the apparent distance. With this, the full, or fully corrected, accommodative convergence, determined by the method 100, can be expressed via the tangent of the corresponding full, or fully corrected, accommodative convergence angle: [α−(δ+φ)/2], in terms of prism diopters Δ. As mentioned earlier, a typical definition of the accommodative convergence is AC=100 tan [α−(δ+φ)/2], in prism diopters Δ. This form shows one of the ways the result of embodiments of the method 100 is a distinct step forward compared to previous methods, where only the disassociated phoria δ was used to correct α, translating into AC=100 tan [α−δ/2]. Another difference compared to previous methods is the particular system 10 and method 100, by which δ was determined.

With the fully corrected AC having been determined by the method 100, the binocular alignment can be again characterized by the AC/A ratio, the ratio of the accommodative convergence AC to the accommodative response A, to characterize the binocular alignment. This AC/A ratio can be determined for a single distance, or can be formed from AC and A values for multiple distances. For brevity, from here on, the fully corrected accommodative convergence AC will be simply referred to as accommodative convergence AC.

In some embodiments, the method 100 can include determining a distance vision accommodative convergence $AC(L_d)$ as an accommodative convergence resulting from performing the method 100 at a distance vision apparent distance $L_d$; and determining a near vision accommodative convergence $AC(L_n)$ as an accommodative convergence resulting from performing the method at a near vision apparent distance $L_n$.

With this preparation, in some embodiments, the binocular alignment of the first eye and the second eye can be characterized by first determining a distance vision accommodative response $A(L_d)$ and a near vision accommodative response $A(L_n)$, in diopters; and then by constructing a ratio of the distance vision accommodative convergence $AC(L_d)$ minus the near vision accommodative convergence $AC(L_d)$, divided by the distance vision accommodative response $A(L_d)$ minus the near vision accommodative response $A(L_n)$, to characterize the binocular alignment of the first eye and the second eye:

$$\text{binocular alignment}=[AC(L_d)-AC(L_n)]/[A(L_d)-A(L_n)] \quad (1)$$

In some embodiments, the measuring 120 at the apparent distance and the determining 140 at the apparent distance can be performed using the accommodation optics 30.

When the drawbacks of existing methods were described earlier, the subjectivity of the patient's feedback has been identified as one source of scatter in the data, and reason for limited reproducibility. In this context, it is mentioned that embodiments of the method 100 can be performed without soliciting a substantive response from the patient to determine one of the key quantities or angles. (Of course, non-substantive responses about, e.g., comfort, can very well be part of the method 100.) This is one of the keys why the method 100 delivers measurements with high reproducibility.

Figure 16:
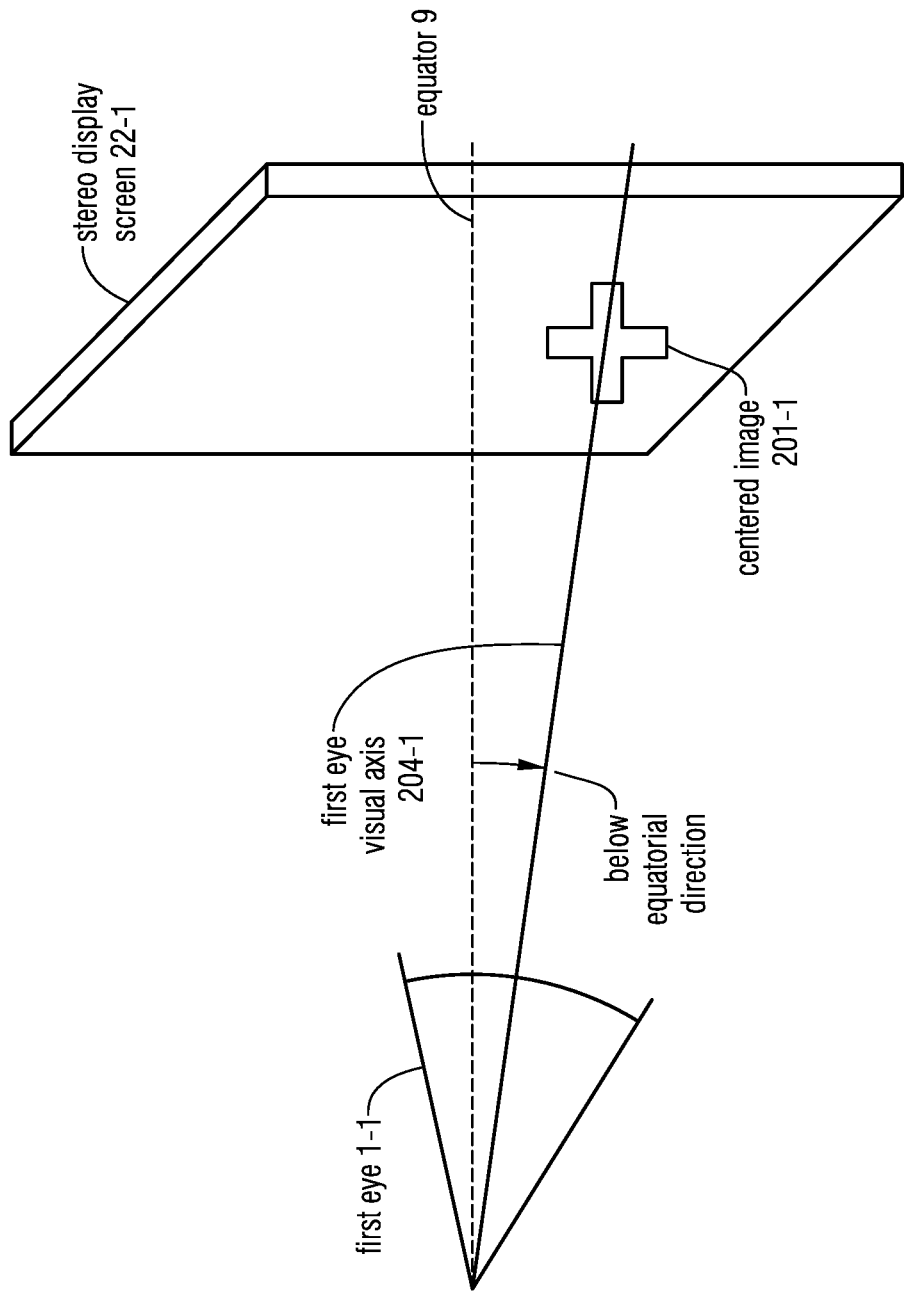
FIG. 16 illustrates a below-the-equator embodiment of the method for determining a binocular misalignment.

FIG. 16 illustrates that in some embodiments, when the method 100 is performed at apparent distances corresponding to near vision, the disassociated phoria and the accommodative convergence corresponding to the near vision can be determined at viewing angles below an equatorial direction 9 by displaying the centered images 201 below the equatorial direction 9.

Applicant's extensive experimentation demonstrated that when prismatic eye glasses were manufactured based on the accommodative convergence determined by the method 100, the patients wearing these glasses reported particularly promising reduction of digital-device related visual discomforts, pains and migraines.

It is quite likely that this substantial improvement has been achieved, among others, because the method 100 developed and integrated solutions regarding the points (1)-(5) identified earlier as follows.

(1) The method 100 does not use the patient's subjective responses as key inputs.
(2) The method 100 uses both peripheral images, e.g. the images 124 and 210, and central images, e.g. the images 201 and 212.
(3) The method 100 uses a two-stage method with the measuring step 120 and the determining step 140, gathering and utilizing information about both central vision and peripheral vision.
(4) The method 100 uses moving test images, e.g. the images 210.
(5) The method 100 developed a particular definition of the accommodative convergence and the protocol for its determination, e.g. in steps 142-156, and proved with extensive testing that eye glasses prescribed using this definition reduce eye-strain related discomfort particularly efficiently.

For all these reason, the above described system 10 and method 100 offer promising new ways to reduce eye-strain related discomfort, pain and migraines.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The invention claimed is:

1. A method to determine a binocular alignment, the method comprising:
measuring a disassociated phoria of a first eye and a second eye of a patient by presenting non-fusible images with a first apparent distance vergence by presenting a target for a first eye and presenting a disassociated targetless image for the second eye with a first apparent distance vergence, and
measuring the disassociated phoria of at least one of the first eye and the second eye in response to the presenting of non-fusible images, using an eye tracker;
determining an accommodative convergence of the first eye and the second eye by presenting fusible images for the first eye and the second eye with the first apparent distance vergence, corrected with the measured disassociated phoria and tracking an adjustment of the first eye and the second eye in response, using the eye tracker;
repeating the measuring the disassociated phoria with a second apparent distance vergence;
repeating the determining the accommodative convergence with the second apparent distance vergence; and
constructing a ratio of a difference of the determined accommodative convergence at the first distance minus at the second distance, divided by a difference of an accommodative response at the first distance minus at the second distance.

2. The method of claim 1, the measuring comprising:
projecting non-fusible images for the first eye and the second eye using a stereo display.

3. The method of claim 2, the projecting comprising:
projecting a dominant image for the first eye; and
projecting a non-dominant image for the second eye.

4. The method of claim 2, the measuring comprising:
measuring the disassociated phoria by measuring an orientation of at least one of the first eye and the second eye in a relaxed state, using the eye tracker.

5. The method of claim 1, the measuring comprising:
projecting a centered image for the first eye with an apparent distance vergence, using a stereo display;
projecting a distributed image for the second eye with an apparent distance vergence, using the stereo display, wherein the centered image and the distributed image are non-fusible;
tracking a rotation of at least one of the first eye and the second eye using the eye tracker;
identifying a relaxed state from a stabilization of the tracked rotation; and
measuring the disassociated phoria by measuring an orientation of at least one of the first eye and the second eye in the relaxed state using the eye tracker and a computer.

6. The method of claim 1, the determining comprising:
presenting a first image for the first eye and a second image for the second eye, with the apparent distance vergence corrected with the measured disassociated phoria, using a stereo display; wherein
the first image and the second image are fusible.

7. The method of claim 6, wherein:
the first image and the second image are peripheral.

8. The method of claim 6, wherein:
the first image and the second image are dynamic.

9. The method of claim 6, wherein:
the first image and the second image are static.

10. The method of claim 6, wherein:
the first image and the second image are central.

11. The method of claim 6, the determining comprising:
projecting a first added central image for the first eye, and
projecting a second added central image for the second eye,
in an alternating manner, using the stereo display.

12. The method of claim 11, the determining comprising:
tracking an adjustment of the first eye in response to the projecting of the first added central image, and
tracking an adjustment of the second eye in response to the projecting of the second added central image, using the eye tracker.

13. The method of claim 12, the determining comprising:
projecting a shifted first added central image with a first iterative associated phoria, to reduce the adjustment of the first eye; and
projecting a shifted second added central image with a second iterative associated phoria to reduce the adjustment of the second eye,
in an alternating manner, using the stereo display and a computer.

14. The method of claim 13, the determining comprising:
tracking an adjustment of the first eye in response to the projecting of the shifted first added central image, and
tracking an adjustment of the second eye in response to the projecting of the shifted second added central image using the eye tracker.

15. The method of claim 14, the determining comprising:
determining whether an effective adjustment of the first and second eye is less than an adjustment threshold.

16. The method of claim 15, the determining comprising:
returning to the projecting the shifted first added central image step if the effective adjustment of the first and second eye is greater than the adjustment threshold; and
identifying a stabilized associated phoria from the last first iterative associated phoria and the last second iterative associated phoria, if the effective adjustment of the first and second eye is less than the adjustment threshold.

17. The method of claim 16, the determining comprising:
identifying a sum of the disassociated phoria and the stabilized associated phoria as a correction to the accommodative convergence, corresponding to the apparent distance.

18. The method of claim 1, wherein:
determining a distance vision accommodative convergence as an accommodative convergence resulting from performing the method at a distance vision apparent distance; and
determining a near vision accommodative convergence as an accommodative convergence resulting from performing the method at a near vision apparent distance.

19. The method of claim 18, comprising:
determining a distance vision accommodative response and a near vision accommodative response; and
constructing a ratio of the distance vision accommodative convergence minus the near vision accommodative convergence, divided by the distance vision accommodative response minus the near vision accommodative response, to characterize the binocular alignment of the first eye and the second eye.

20. The method of claim 18, the determining a near vision accommodative convergence comprising:
determining the near vision accommodative convergence at viewing angles below an equatorial direction.

21. The method of claim 1, wherein:
performing the method without soliciting a response from the patient.

* * * * *